United States Patent
Sakai et al.

[11] Patent Number: 5,976,516
[45] Date of Patent: Nov. 2, 1999

[54] HAIR COSMETIC COMPOSITIONS

[75] Inventors: Masahiko Sakai; Kumi Sugino; Yuji Hirano, all of Tokyo, Japan

[73] Assignee: Kao Corporation, Tokyo, Japan

[21] Appl. No.: 08/966,019

[22] Filed: Nov. 7, 1997

[30] Foreign Application Priority Data

Nov. 22, 1996 [JP] Japan ................................. 8-312467
Nov. 22, 1996 [JP] Japan ................................. 8-312468

[51] Int. Cl.$^6$ ................................. A61K 7/06; A61K 7/00
[52] U.S. Cl. ........................... 424/70.1; 424/401; 514/613
[58] Field of Search ................. 424/70.1, 401; 514/613

[56] References Cited

U.S. PATENT DOCUMENTS

| | | | |
|---|---|---|---|
| 5,182,033 | 1/1993 | Lagerman | 252/8.6 |
| 5,198,210 | 3/1993 | Critchley et al. | 424/78.03 |
| 5,439,615 | 8/1995 | Lefebvre et al. | 252/548 |
| 5,476,671 | 12/1995 | Cho et al. | 424/70.1 |
| 5,618,523 | 4/1997 | Zysman et al. | 424/70.1 |
| 5,641,495 | 6/1997 | Jokura et al. | 424/401 |

*Primary Examiner*—Sally Gardner-Lane
*Attorney, Agent, or Firm*—Oblon, Spivak, McClelland, Maier & Neustadt, P.C.

[57] ABSTRACT

Described is a hair cosmetic composition comprising an amide compound having a melting point of 0 to 50° C. The hair cosmetic composition according to the present invention can impart the hair with suppleness, improve the touch feeling and bring about spilt hair preventive effects. Concerning the touch feeling, in particular, the composition can impart the hair with natural feeling, more specifically, with moisturized feeling, finger passing ease, styling ease, luster and not greasy but good oily feeling, whereby the hair with healthy, moisturized and young impression can be obtained.

17 Claims, No Drawings

HAIR COSMETIC COMPOSITIONS

BACKGROUND OF THE INVENTION

1. Field of the Invention

The present invention relates to a hair cosmetic composition which can impart hair with suppleness and improve the touch feeling.

2. Description of the Related Art

Various changes in the hair conditions such as deterioration in the touch feeling, for example, loss of moisturized touch feeling from hair, and weakening of hair strength have generally been recognized as hair troubles. These changes in the physical properties of hair are presumed to occur because of the mechanical or chemical treatment usually given to hair for a long period of time. With a view to overcoming the deterioration in the touch feeling of hair, for example, loss of moisturized touch feeling from hair, the addition of an oily ingredient to a hair cosmetic composition has been adopted as one measure.

The oily ingredient is however accompanied with the problems that it imparts hair with greasy touch feeling and heavy looking and instead of improving the smoothness, it arouses somewhat resistance against combing or finger combing.

SUMMARY OF THE INVENTION

An object of the present invention is therefore to provide a hair cosmetic composition which can suppress a loss of moisturized touch feeling from hair, style hair firmly and improve the touch feeling.

With the forgoing in view, the present inventors have carried out an extensive investigation. As a result, it has been found that the use of a specific amide compound makes it possible to provide a hair cosmetic composition which can prevent the lift-up phenomenon of hair cuticle and retard the progress of hair damage, and thereby is capable of imparting hair with suppleness, styling the hair firmly, and improving the touch feeling of the hair, leading to the completion of the invention.

In the present invention, there is thus provided a hair cosmetic composition comprising an amide compound having a melting point ranging from 0 to 50° C.

A further object of the present invention is to provide the use of the same amide compound for preventing the lift-up phenomenon of hair cuticle and retarding the progress of hair damage.

The hair cosmetic composition according to the present invention can impart hair with suppleness, thereby styling the hair firmly, and improve the touch feeling and besides, has effects for preventing spilt hair. Concerning the touch feeling, the hair cosmetic composition can impart hair with moisturized touch feeling, smoothness with easy finger passing, styling ease, luster and favorable oily touch feeling free of greasiness. Thus, the hair treated with the composition has a healthy and fresh looking with natural touch feeling, thus giving a younger impression.

Moreover, by treating hair with the hair cosmetic composition of the present invention in repetition, the effective ingredient contained therein penetrates into hair, thereby bringing about high hair quality improving effects.

DETAILED DESCRIPTION OF THE PREFERRED EMBODIMENTS

The amide compound usable in the present invention has a melting point ranging from 0 to 50° C., preferably 10 to 40° C. The amide compounds having the melting point outside the above range cannot be incorporated in the composition stably.

In the present invention, incidentally, the melting point is indicated by an extrapolation melt starting point as measured in accordance with JIS-K-7121-1987-9-9.1(2).

Examples of such an amide compound include acid amides such as isostearic acid amide, isopalmitic acid amide, isomyristic acid amide and phytostearyl acylglutamate and amide derivatives represented by the following formulas (1) to (3):

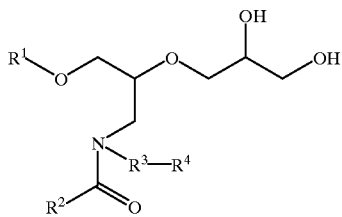

wherein $R^1$ and $R^2$ are the same or different and each independently represents a $C_{1-40}$ hydrocarbon group which may be hydroxylated, $R^3$ represents a linear or branched $C_{1-6}$ alkylene group or a single bond, and $R^4$ represents a hydrogen atom, a linear or branched $C_{1-12}$ alkoxy group or a 2,3-dihydroxypropyloxy group, with the proviso that when $R^3$ represents a single bond, $R^4$ is a hydrogen atom.

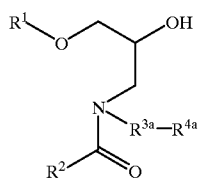

wherein $R^1$ and $R^2$ have the same meanings as defined above, $R^{3a}$ represents a linear or branched $C_{3-6}$ alkylene group, and $R^{4a}$ represents a linear or branched $C_{1-12}$ alkoxy group.

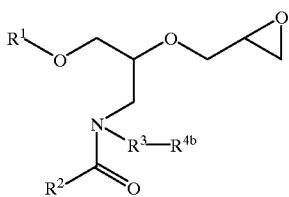

wherein $R^1$, $R^2$ and $R^3$ have the same meanings as defined above, and $R^{4b}$ represents a hydrogen atom, a linear or branched $C_{1-12}$ alkoxy group or a 2,3-epoxypropyloxy group, with the proviso that when $R^3$ represents a single bond, $R^{4b}$ is a hydrogen atom.

In the amide derivative (1), among these amide derivatives, $R^1$ and $R^2$ are the same or different and each independently represents a linear or branched, saturated or unsaturated $C_{1-40}$ hydrocarbon group which may be hydroxylated. Examples of $R^1$ and $R^2$ include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, heneicosyl, docosyl, nonacosyl, triacontyl, isostearyl, isoheptadecyl, 2-ethylhexyl, 1-ethylheptyl, 8-heptadecyl, 8-heptadecenyl, 8,11-heptadecadienyl, 2-heptylundecyl, 9-octadecenyl, 1-hydroxynonyl, 1-hydroxypentadecyl, 2-hydroxypentadecyl, 15-hydroxypentadecyl, 11-hydroxyheptadecyl and 11-hydroxy-8-heptadecenyl.

As $R^1$, linear or branched $C_{8-26}$ alkyl or alkenyl groups are preferred and specific examples include octyl, decyl, dodecyl, tetradecyl, hexadecyl, octadecyl, docosyl, triacontyl, isostearyl, 2-ethylhexyl, 2-heptylundecyl and 9-octadecenyl. Particularly preferred hydrocarbon groups as $R^1$ are linear or branched $C_{12-22}$ alkyl groups such as dodecyl, tetradecyl, hexadecyl, octadecyl, docosyl and methyl-branched isostearyl.

As $R^2$, linear or branched $C_{9-25}$ alkyl or alkenyl groups are preferred. Specific examples include nonyl, undecyl, tridecyl, pentadecyl, heptadecyl, heneicosyl, nonacosyl, isoheptadecyl, 1-ethylheptyl, 8-heptadecyl, 8-heptadecenyl, 8,11-heptadecadienyl, 1-hydroxynonyl, 1-hydroxypentadecyl, 2-hydroxypentadecyl, 15-hydroxypentadecyl, 11-hydroxyheptadecyl and 11-hydroxy-8-heptadecenyl groups. Particularly preferred hydrocarbon groups as $R^2$ are linear or branched $C_{11-21}$ alkyl groups such as undecyl, tridecyl, pentadecyl, heptadecyl, heneicosyl and methyl-branched isoheptadecyl groups.

$R^3$ represents a linear or branched $C_{1-6}$ alkylene group or a single bond. Illustrative alkylene groups include methylene, ethylene, trimethylene, tetramethylene, pentamethylene, hexamethylene, 1-methylethylene, 1-methyltrimethylene, 2-methyltrimethylene, 1,1-dimethylethylene, 1-ethylethylene, 1-methyltetramethylene, 2-ethyltrimethylene groups. As $R^3$, linear $C_{1-6}$ alkylene groups are preferred, with methylene, ethylene and trimethylene being particularly preferred.

$R^4$ represents a hydrogen atom, a linear or branched $C_{1-12}$ alkoxy group or a 2,3-dihydroxypropyloxy group. Illustrative alkoxy groups include methoxy, ethoxy, propoxy, butoxy, hexyloxy, octyloxy, decyloxy, 1-methylethoxy and 2-ethylhexyloxy groups. As $R^4$, preferred are a hydrogen atom, $C_{1-8}$ alkoxy groups and a 2,3-dihydroxypropyloxy group, with a hydrogen atom, and methoxy, ethoxy, propoxy, butoxy, 1-methylethoxy, 2-ethylhexyloxy and 2,3-dihydroxypropyloxy groups being particularly preferred.

As an amide derivative (1), particularly preferred are compounds having the formula (1) in which $R^1$, $R^2$, $R^3$ and $R^4$ are those selected in combination from the above-described particularly preferred ranges.

In the amide derivative (2), $R^1$ and $R^2$ have the same meanings as described above and the same groups are preferably used. Examples of $R^{3a}$ are similar to the alkylene groups exemplified as $R^3$ in the amide derivative (1) except for the omission of methylene and ethylene. As $R^{3a}$, linear $C_{3-6}$ alkylene groups are preferred, with trimethylene being particularly preferred. Examples of $R^{4a}$ are similar to the alkoxy groups as exemplified as $R^4$ in the amide derivative (1). Preferred examples are also similar to those of $R^4$ in (1).

In the amide derivative (3), $R^1$, $R^2$ and $R^3$ have the same meanings as defined above. $R^{4b}$ represents a hydrogen atom, a linear or branched $C_{1-12}$ alkoxy group or a 2,3-epoxypropyloxy group. Specific examples of $R^1$, $R^2$ and $R^3$ are similar to those exemplified above with respect to the amide derivative (1). Their preferred examples are similar to those mentioned above. Examples of the linear or branched $C_{1-12}$ alkoxy group as $R^{4b}$ are similar to those of $R^4$ in the amide derivative (1). Specifically, a hydrogen atom, alkoxy groups similar to those exemplified above as $R^4$ and a 2,3-epoxypropyloxy group are preferred.

Among the amide derivatives (1) to (3), those represented by the formula (1) are particularly preferred.

The amide derivative (1) can be obtained, for example, by the following Preparation Process 1 or Preparation Process 2.

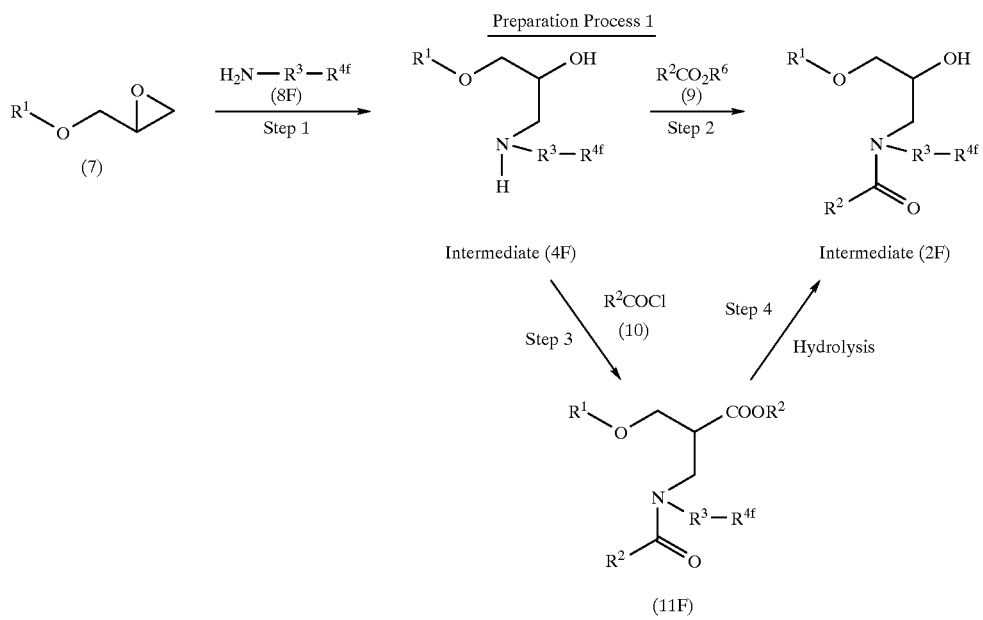

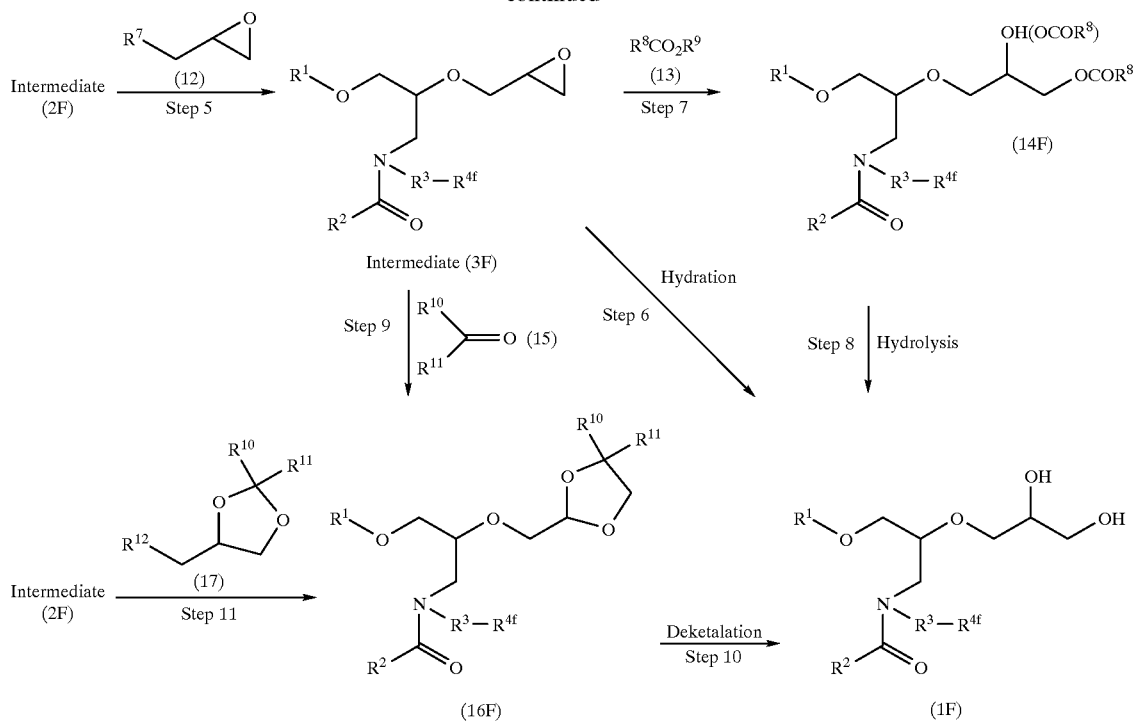

wherein $R^1$, $R^2$ and $R^3$ have the same meanings as defined above; $R^{4f}$ represents a hydrogen atom or a linear or branched $C_{1-12}$ alkoxy group, with the proviso that $R^4$ is a hydrogen atom when $R^3$ represents a signal bond; $R^6$, $R^8$, $R^{10}$ and $R^{11}$ individually represent a linear or branched, saturated or unsaturated $C_{1-8}$ hydrocarbon group, with a linear or branched $C_{1-5}$ alkyl group being preferred and with a methyl group being particularly preferred; $R^9$ represents a hydrogen atom, an alkali metal atom or a $COR^8$ group; and $R^7$ and $R^{12}$ individually represent an eliminative atom or group such as halogen atom, mesylate group or tosylate group. From the standpoint of availability and the like, $R^7$ is preferably a chlorine atom or bromine atom, with a chlorine atom being particularly preferred. From the stand-point of availability and the like, $R^{12}$ is preferably a mesylate group or tosylate group.

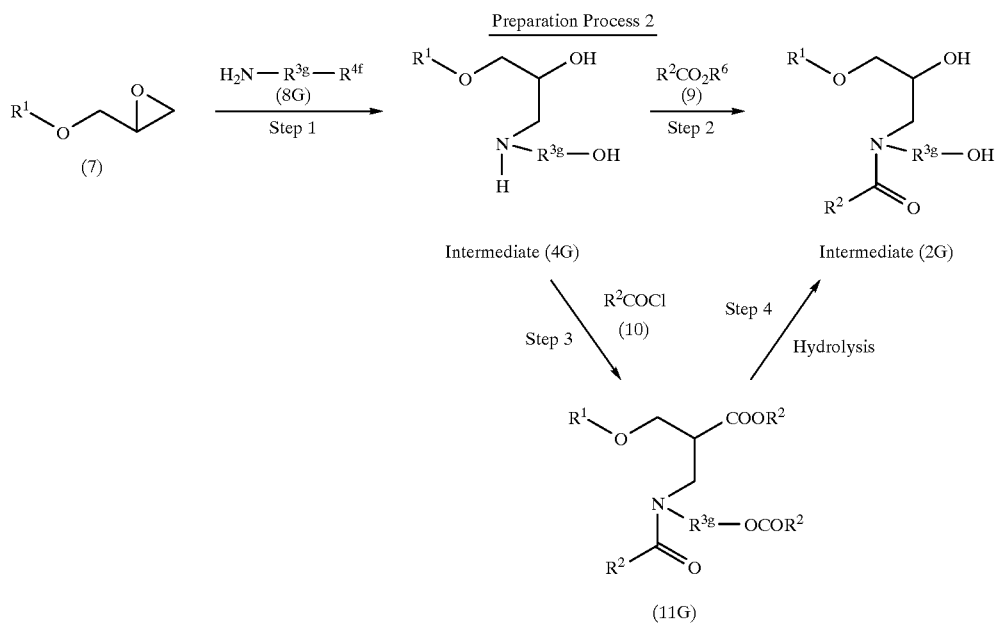

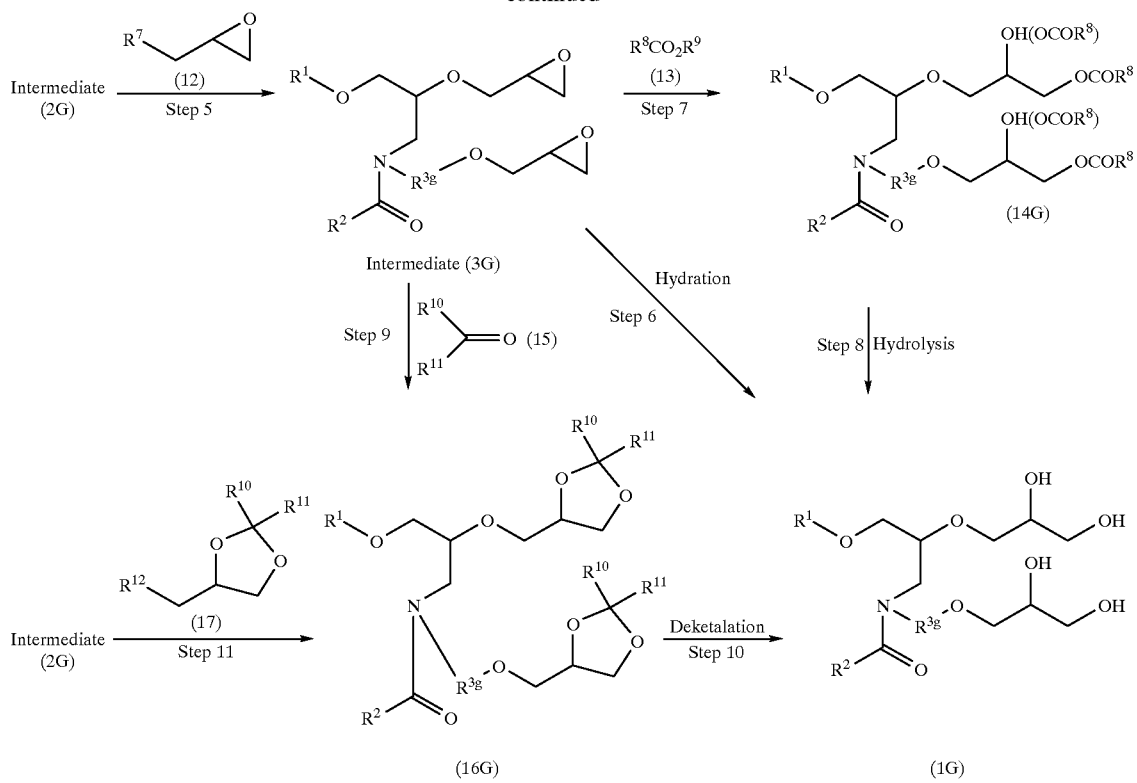

wherein $R^1$, $R^2$, $R^6$ to $R^{12}$ have the same meanings as defined above, and $R^{3g}$ represents a linear or branched alkylene group having 1 to 6 carbon atoms.

Reaction conditions for the individual steps of the Preparation Process 1 and Preparation Process 2 are as follows:

Step 1

An amino alcohol derivative (4F) or (4G) can be prepared by reacting a glycidyl ether (7) and an amine (8F) or (8G) at room temperature to 150° C. either in a solventless manner or in a solvent, for example, water, a lower alcohol such as methanol, ethanol or isopropanol, an ether solvent such as tetrahydrofuran, dioxane or ethylene glycol dimethyl ether, a hydrocarbon solvent such as hexane, benzene, toluene or xylene, or a mixed solvent of desired two or more solvents thereof.

Step 2

An amide derivative (2F) or (2G) can be prepared by reacting the amino alcohol derivative (4F) or (4G) with a fatty acid ester (9), preferably a lower alkyl ester of a fatty acid such as the methyl ester of a fatty acid or the ethyl ester of a fatty acid under a reduced pressure of from normal pressure to 0.01 mmHg at room temperature to 150° C. in the presence of a basic catalyst, for example, an alkali metal hydroxide such as potassium hydroxide or sodium hydroxide, an alkaline earth metal hydroxide such as calcium hydroxide, an alkali metal carbonate such as potassium carbonate, an alkaline earth metal carbonate such as calcium carbonate, or an alkali metal alcoholate such as sodium methoxide, sodium ethoxide or potassium tert-butoxide. Here, the basic catalyst may be used preferably in an amount of 0.01 to 0.2 equivalent based on the amino alcohol derivative (4F) or (4G). It is preferred to conduct the reaction while taking the resulting alcohol out of the system, as the reaction is allowed to proceed at a higher velocity.

Step 3

The amide derivative (2F) or (2G) can also be prepared by reacting the amino alcohol derivative (4F) or (4G) with a fatty acid chloride (10) at room temperature to 100° C. either in a solventless manner or in a solvent, for example, a halogenated hydrocarbon solvent such as chloroform, methylene chloride or 1,2-dichloroethane, an ether solvent such as tetrahydrofuran, dioxane or ethylene glycol dimethyl ether, a hydrocarbon solvent such as hexane, benzene, toluene or xylene or in a mixed solvent of desired two or more solvents thereof in the presence or absence of a base, for example, a tertiary amine such as pyridine or triethylamine to convert the amino alcohol derivative (4F) or (4G) into an amide ester derivative (11F) or (11G) and then, Step 4 by selectively hydrolyzing its ester group under basic conditions, for example, in the presence of an alkali metal hydroxide such as potassium hydroxide or sodium hydroxide, an alkaline earth metal hydroxide such as calcium hydroxide, an alkali metal carbonate such as potassium carbonate, an alkaline earth metal carbonate such as calcium carbonate or an alkali metal alcoholate such as sodium methoxide, sodium ethoxide or potassium tert-butoxide.

Step 5

An amide derivative (3F) or (3G) can be prepared by reacting, at room temperature to 150° C., the amide derivative (2F) or (2G) with 1 to 20 equivalents of an epoxide (12), preferably epichlorohydrin either in a solventless manner or in a solvent, for example, water, an ether solvent such as tetrahydrofuran, dioxane or ethylene glycol dimethyl ether, a hydrocarbon solvent such as hexane, benzene, toluene or xylene or a mixed solvent of desired two or more solvents thereof in the presence of 1 to 10 equivalents of an alkali metal hydroxide such as potassium hydroxide or sodium hydroxide, an alkaline earth metal hydroxide such as calcium hydroxide, an alkali metal carbonate such as potassium carbonate or an alkaline earth metal carbonate such as calcium carbonate. From the standpoint of its yield and the like, it is preferred to conduct the reaction in the presence of a phase transfer catalyst, for example, a quaternary ammonium salt such as tetrabutylammonium bromide, tetrabutylammonium chloride, hexadecyltrimethylammonium chloride, hexadecyltrimethylammonium bromide, stearyltrimethylammonium chloride or bis-tetraoxyethylene stearylmethylammonium chloride, or a betaine such as lauryldimethylcarboxyammonium betaine.

Step 6

An amide derivative (1F) or (1G) can be prepared by hydrating the amide derivative (3F) or (3G) at room temperature to 300° C. under basic conditions, for example, in the presence of an alkali metal hydroxide such as potassium hydroxide or sodium hydroxide, an alkaline earth metal hydroxide such as calcium hydroxide, an alkali metal carbonate such as potassium carbonate or an alkaline earth metal carbonate such as calcium carbonate, under acidic conditions, for example, in the presence of a mineral acid such as sulfuric acid or hydrochloric acid, a Lewis acid such as boron trifluoride or tin tetrachloride, a carboxylic acid such as acetic acid, tetradecanoic acid or hexadecanoic acid or a sulfonic acid such as p-toluenesulfonic acid, or under mixed base-acid conditions.

Step 7

The amide derivative (1F) or (1G) can also be prepared by reacting the amide derivative (3F) or (3G) with one or more carboxylic acid derivatives (13), preferably lower fatty acids such as acetic acid, alkali metal salts of lower fatty acids such as sodium acetate, lower fatty acid anhydrides such as acetic anhydride either singly or in combination in the presence or absence of a basic catalyst, for example, a tertiary amine such as triethylamine to convert the amide derivative (3F) or (3G) into an ester-amide derivative (14F) or (14G) and then, Step 8 by selectively hydrolyzing its ester group under basic conditions, for example, in the presence of an alkali metal hydroxide such as potassium hydroxide or sodium hydroxide, an alkaline earth metal hydroxide such as calcium hydroxide, an alkali metal carbonate such as potassium carbonate, an alkaline earth metal carbonate such as calcium carbonate or an alkali metal alcoholate such as sodium methoxide, sodium ethoxide or potassium tert-butoxide.

Step 9

The amide derivative (1F) or (1G) can also be prepared by reacting the amide derivative (3F) or (3G) with a carbonyl compound (15), preferably a lower aliphatic ketone such as acetone or methyl ethyl ketone in the presence of an acid catalyst, for example, a mineral acid such as sulfuric acid, hydrochloric acid or phosphoric acid, a carboxylic acid such as acetic acid, or Lewis acid such as boron trifluoride or tin tetrachloride to convert the amide derivative (3F) or (3G) into a 1,3-dioxolane-amide derivative (16F) or (16G) and then, Step 10 by subjecting the 1,3-dioxolane-amide derivative (16F) or (16G) to deketalation under acidic conditions, for example, in the presence of a mineral acid such as sulfuric acid, hydrochloric acid or phosphoric acid, a carboxylic acid such as acetic acid or a sulfonic acid such as p-toluenesulfonic acid.

Step 11

The 1,3-dioxolane-amide derivative (16F) or (16G) can also be prepared by reacting the amide derivative (2F) or (2G) with a glycerol derivative (17) in the presence of a base, for example, an alkali metal hydroxide such as potassium hydroxide or sodium hydroxide, an alkaline earth metal hydroxide such as calcium hydroxide, an alkali metal carbonate such as potassium carbonate, an alkaline earth metal carbonate such as calcium carbonate or an alkali metal hydride such as sodium hydride either in a solventless manner or in a solvent, for example, an aprotic polar solvent such as N,N-dimethylformamide or dimethylsulfoxide, an ether solvent such as tetrahydrofuran, dioxane or ethylene glycol dimethyl ether, a hydrocarbon solvent such as hexane, benzene, toluene or xylene, or a mixed solvent of desired two or more solvents thereof.

The amide derivative (1) which has been obtained as described above can be purified by a method in a manner known per se in the art. In the present invention, the amide derivative (1) can be used either in the form of a compound purified to 100% purity or in the form of a mixture of a purity of 70% or higher but lower than 100% containing one or more intermediates and/or one or more reaction byproducts while assuring excellent effects and performance without safety problem. It is to be noted that the amide derivative (1) include its solvates typified by its hydrate.

Examples of the amide derivative (1) which can be obtained following the Preparation Process 1 include the following compounds:

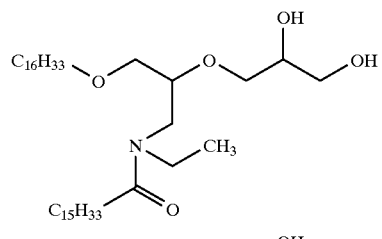

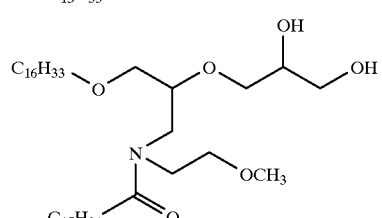

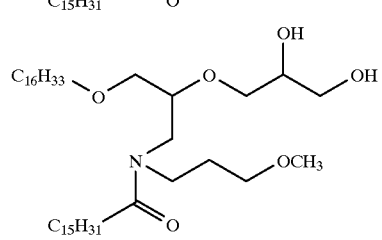

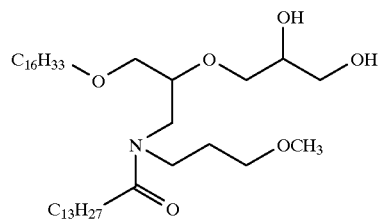

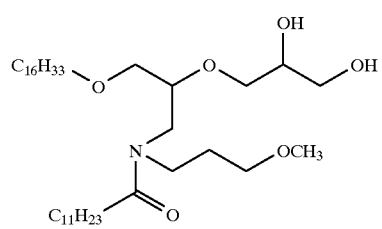

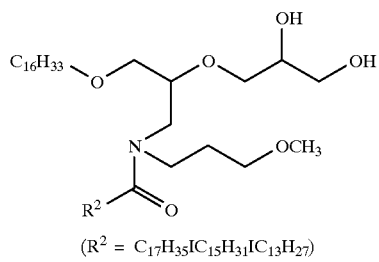

(R² = C₁₇H₃₅IC₁₅H₃₁IC₁₃H₂₇)

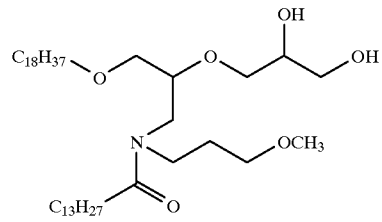

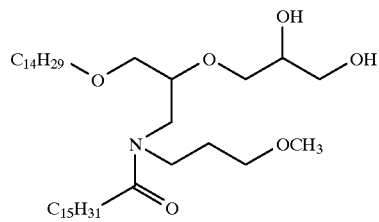

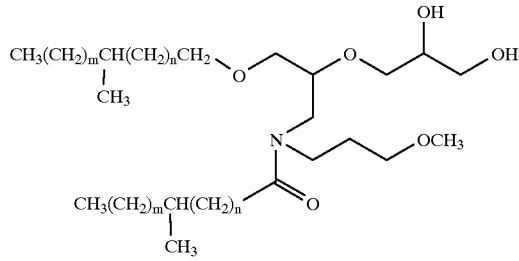

wherein m and n have the same meanings as defined above.

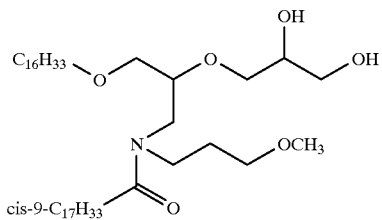

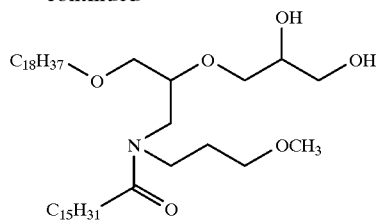

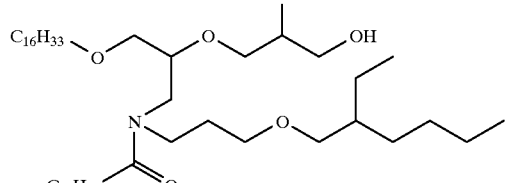

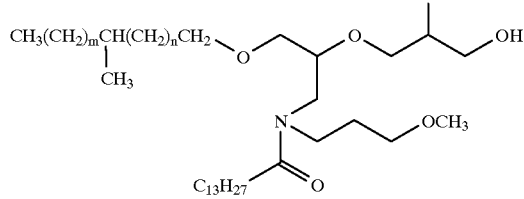

wherein m and n represents numerals having distributions centered at m=7 and n=7 with m+n in a range of from 10 to 16, m in a range of from 4 to 10 and n in a range of from 4 to 10.

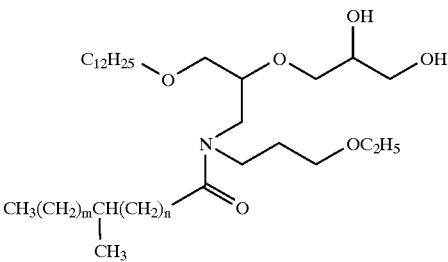

wherein m and n have the same meanings as defined above.

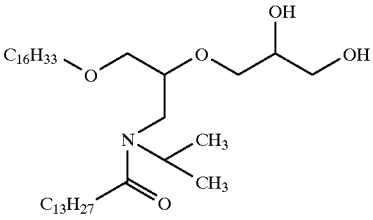

Examples of the amide derivative (1) which can be obtained following the Preparation Process 2 include the following compounds:

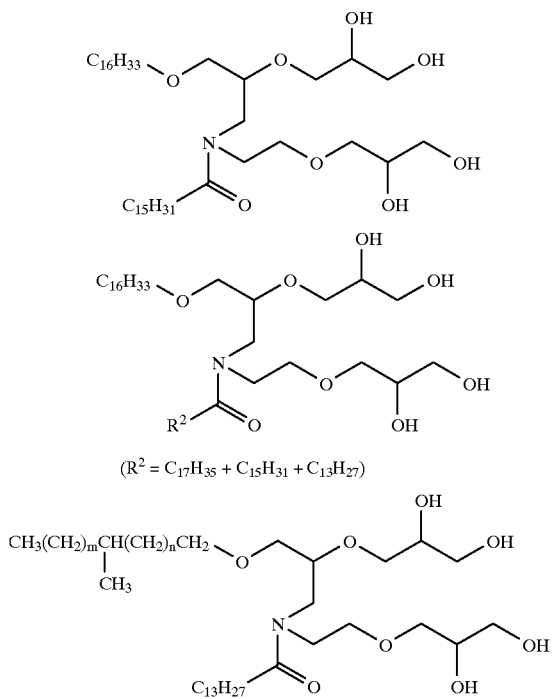

wherein m and n represent numerals having distributions centered at m=7 and n=7 with m+n in a range of from 10 to 16, m in a range of from 4 to 10 and n in a range of from 4 to 10.

As the amide compound, N-substituted amide compounds having at least 30 carbon atoms in total are particularly preferred, because such compounds have a high binding property with water and therefore bring about an improvement in the penetration into hair.

Besides, as the amide compound, those capable of retaining bound water in an amount of 1 wt. % or greater, particularly 5 wt. %, or greater are preferred. Here, the content of bound water can be determined by adding water to the sample at room temperature, measuring as the amount of bound water the maximum amount of water that can be added until a uniform phase is lost, and finding the percentage of the total amount of the bound water to the total amount of the sample in accordance with the following formula:

$$\frac{\text{Total amount of water (g)}}{\text{Total amount of the sample (g)}} \times 100 = \text{bound water content (wt. \%)}$$

The above amide compounds can be used either singly or in combination. The amide compound is preferably added in an amount of 0.001 to 50 wt. % based on the whole composition. Particularly, when it is added in an amount of 0.01 to 40 wt. %, preferably 0.1 to 20 wt. %, hair free of stickiness and with suppleness can be obtained. Such an amount is therefore preferred.

By incorporating, in addition to the above ingredient, a sterol in the hair cosmetic composition of the present invention, it is possible to impart the hair with strength and body and hardness. This effect is markedly important, because many persons have complaint of the weakening of hair, in other words, lowering in the strength and body of hair as hair troubles.

Examples of the sterol usable in the present invention include cholesterol and cholesterol derivatives. Specific examples of the cholesterol derivative include cholesteryl alkenylsuccinate, cholesteryl esters containing a saturated or unsaturated, linear or branched $C_{12-36}$, preferably, $C_{14-28}$ hydrocarbon group and dehydrocholesterol. As the cholesteryl alkenylsuccinate, those synthesized by a preparation process described in Japanese Patent Laid-Open No. HEI 5-294989, for example, cholesteryl n-hexadecenylsuccinate monoester and cholesteryl n-octadecenylsuccinate monoester can be given as examples. Illustrative cholesteryl esters include cholesteryl isostearate, cholesteryl 1,2-hydroxystearate, cholesteryl ester of lanolin fatty acid and cholesteryl ricinoleate. Among them, cholesteryl alkenylsuccinate, cholesterol and cholesteryl isostearate are preferred.

The above-exemplified sterols can be used either singly or in combination. It is preferred to add in an amount of 0.001 to 40 wt. % based on the total weight of the composition, with 0.01 to 20 wt. % being particularly preferred and with 0.1 to 10 wt. % being still more preferred.

To the hair cosmetic composition according to the present invention, an oily ingredient can be added further. The addition of it brings about an improvement or adjustment of the touch feeling and is therefore preferred. No particular limitation is imposed on the oily ingredient insofar as it is used for the conventional cosmetic compositions. Examples include hydrocarbons, waxes, animal or vegetable fats and oils, higher alcohols, higher fatty acids, amide amines, glycerins, esters, ethers and silicones.

Described specifically, examples of the hydrocarbon include liquid paraffin, squalene, vaseline and solid paraffin, those of the waxe include beeswax, sperm wax, lanolin and carnauba wax and those of the animal or vegetable fats and oils include castor oil, cacao oil, mink oil, avocado oil, olive oil and macadamia nut oil.

Examples of the higher alcohol include higher alcohols containing a linear or branched alkyl or alkenyl group such as cetyl alcohol, oleyl alcohol, stearyl alcohol, arachidic alcohol, behenyl alcohol, hexadecyl alcohol, lauryl alcohol, isostearyl alcohol and 2-octyldodecanol.

Examples of the higher fatty acid include stearic acid, myristic acid, behenic acid, isostearic acid, 18-methyleicosanoic acid and coconut oil fatty acid, those of the amide amine include longer chain amide amines containing a linear or branched alkyl or alkenyl group, and those of the glycerin include propylene glycol and glycerin.

Examples of the ester include esters of a higher fatty acid such as isopropyl myristate, isopropyl laurate, isopropyl palmitate, hexyl laurate, cetyl lactate, propylene glycol monostearate, oleyl oleate, hexadecyl 2-ethylhexanoate, octyldodecyl myristate, trimethylhexanyl trimethyl hexanoate, isononyl isononanoate and tridecyl isononanoate; higher fatty acid/cholesterol esters such as cholesteryl 12-isostearate and cholesteryl esters of macadamia nut fatty acid; and higher fatty acid/glycerin esters such as monoglyceride oleate, glyceride palmitate, monoglyceride behenate and monoglyceride isostearate.

Examples of the ether include isostearyl glyceryl ether, polyoxyethylene propylene butyl ether and isostearyl cholesteryl ether.

As the silicones, those exemplified below in (a) to (h) can be given as examples.

(a) Polyether modified silicones represented by the formulas (21) to (24):

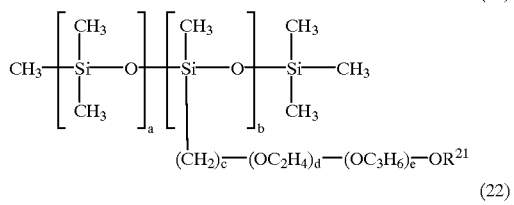
(21)

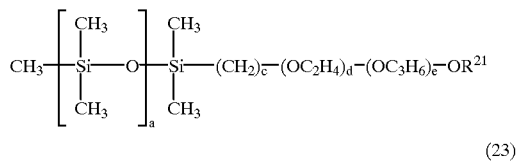
(22)

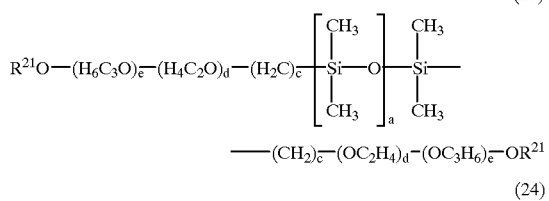
(23)

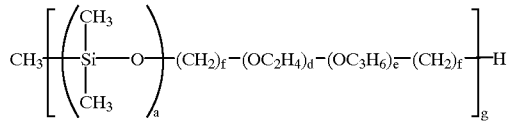
(24)

wherein $R^{21}$ represents a hydrogen atom or a $C_{1-10}$ hydrocarbon group, a stands for 15 or greater, b stands for 1 or greater, c stands for 1 to 6, d stands for 1 to 300, e stands for 0 to 300, f stands for 0 to 6 and g stand for 2 to 500.

As the hydrocarbon group represented by $R^{21}$, linear or branched, saturated $C_{1-8}$ hydrocarbon groups are preferred, with a methyl group being particularly preferred. In the above formula, a stands for 20 to 500, b stands for 1 to 100, c stands for 2 to 4, d stands for 2 to 50, e stands for 0 to 50, f stands for 2 to 4 and g stands for 2 to 50.

When a stands for a number smaller than 15, excellent finish feeling cannot be attained and therefore, such a number is not preferred.

As polyether-modified silicones, commercially available ones can be used suitably. Preferred examples include "SH3772C", "SH3773C" and "SH3775C" (each, trade name; product of Dow Coning Toray Silicone Co., Ltd.); "KF352A", "KF353A", "KF615A" and "KF945A" (each, trade name; product of Shin-Etsu Chemical Co., Ltd.) and "Silwet L-70001", "L-7002" and "L-7602" (each, trade name; product of Nippon Unicar Co., Ltd.).

(b) Dimethyl polysiloxane, methylphenyl polysiloxane or diphenyl polysiloxane represented by the formula (25):

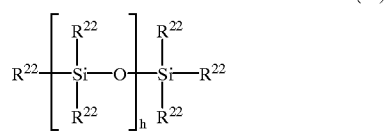
(25)

wherein $R^{22}$s are the same or different and each independently represents a methyl group, a phenyl group or —OSi$(CH_3)_2$ and h stands for 3 or greater.

In the above formula, a methyl group is preferred as $R^{22}$ and 50 to 3000 is preferred as h.

Among the above-exemplified polysiloxanes, dimethyl polysiloxane is particularly preferred. For example, commercially-available products such as "SH 200 Series" (having a viscosity of at least 100 cs) and "BY11-004" (each, trade name; product of Dow Coning Toray Silicone Co., Ltd.); and "KF 96 Series" (having a viscosity of at least 100 cs), "KF96H Series" and "X-21-7501G" (each, trade name; product of Shin-Etsu Chemical Co., Ltd.) can be used suitably.

(c) (Longer chain)alkyl-modified silicones represented by the following formula (26):

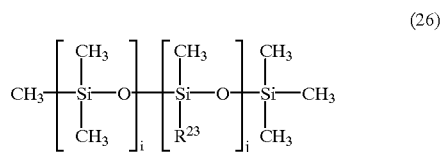
(26)

wherein $R^{23}$ represents a $C_{10-50}$ hydrocarbon group, i stands for 0 to 1000 and j stands for 1 to 1000.

In the above formula, a linear or branched, saturated $C_{15-40}$ hydrocarbon group is preferred as the hydrocarbon group represented by $R^{23}$, 10 to 500 is preferred as i and 10 to 500 is preferred as j.

(d) Alkoxy-modified silicones represented by the formula (27):

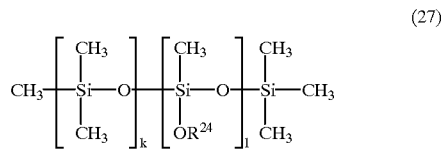
(27)

Wherein $R^{24}$ represents a $C_{10-30}$ hydrocarbon group, k stands for 3 to 100 and l stands for 1 to 50.

As the hydrocarbon group represented by $R^{24}$, linear or branched, saturated $C_{12-20}$ hydrocarbon groups are preferred, with cetyl and stearyl groups being particularly preferred. As k, 5 to 50 and as l, 2 to 20 are preferred, respectively.

(e) Amino-modified silicones represented by the formula (28):

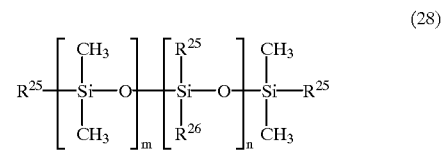
(28)

wherein $R^{25}$s are the same or different and each independently represents a hydrogen atom, a hydroxyl group, a methyl group or a methoxy group, $R^{26}$ represents —$(CH_2)_o$—$(OC_2H_4)_p$—$(OC_3H_6)_q$—$(NHC_2H_4)N(R^{27})_2$ or —$(CH_2)_o$—$(OC_2H_4)_p$—$(OC_3H_6)_q$—$(NHC_2H_4)N^+(R^{27})_3.Z^-$, in which $R^{27}$s are the same or different and each independently represents a hydrogen atom or a $C_{1-6}$ hydrocarbon group, Z represents a halogen ion or an organic anion, o stands for 1 to 6 and p and q individually represent 0 to 6, m stands for 3 to 300 and n stands for 1 to 50.

In the above formula, preferred are hydroxyl and methyl groups as $R^{25}$, —$(CH_2)_3$—$NHC_2H_4NH_2$ as $R^{26}$, 3 to 300 as m and 1 to 20 as n.

(f) Butene-salt-modified silicones represented by the formula (29) or (30):

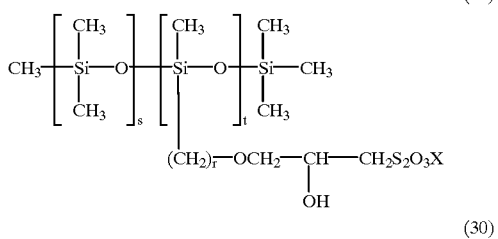

(29)

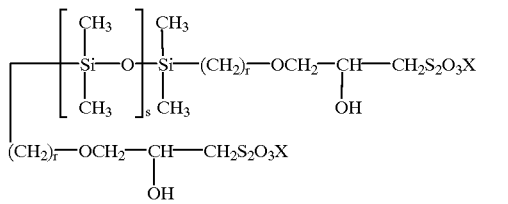

(30)

wherein X represents an alkali metal, alkaline earth metal, ammonia, amine or quaternary ammonium salt, r stands for 1 to 6 and s and t individually represent 1 to 20 and at the same time, s/t is greater than 1.

In the above formula, preferred are alkali metals such as sodium and potassium and quaternary ammonium salts as X, 2 to 4 as r and 5 to 20 as s and t.

(g) Silicone resins represented by the formula (31):

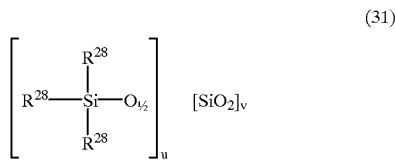

(31)

wherein $R^{28}$ s are the same or different and each independently represents a methyl or phenyl group, u and v individually represent 10 to 100 and at the same time, u/v represents 0.1 to 10.

In the above formula, preferred as $R^{28}$ is a methyl group and preferred as u and v are 10 to 50, respectively.

(h) Oxazoline-modified silicone elastomers

Examples of the oxazoline-modified silicone elastomer include organopolysiloxanes each of which has a poly(N-acylalkyleneimine) bound with at least one silicon atom at the terminal or side chain of the organopolysiloxane segment through an hetero-atom-containing alkylene group, said poly(N-acylalkyleneimine) being composed of recurring units each represented by the following formula:

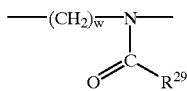

wherein $R^{29}$ represents a hydrogen atom, a $C_{1-22}$ alkyl, aralkyl or aryl group and w stands for 2 or 3; comprises the organopolysiloxane segment and the poly(N-acylalkyleneimine) at the weight ratio ranging of from 98:2 to 40:60; and has a weight average molecular weight of 50,000 to 500,000.

Among the above-exemplified oily ingredients, hydrocarbons, esters and silicones are preferred, with liquid paraffin, squalene, isopropyl myristate and octyldodecyl myristate being more preferred.

The above oily ingredients can be used either singly or in combination. It is preferred to add it in an amount of 0.001 to 50 wt. % based on the total amount of the composition, with 0.01 to 40 wt. % being particularly preferred and with 0.1 to 20 wt. % being still more preferred.

To the hair cosmetic composition of the present invention, a polymer can be added further. Addition of the polymer even in a small amount makes it possible to impart hair with strength and body, heighten the effects of the oily ingredient and also heighten the stability. The use of it is therefore desired. No particular limitation is imposed on such a polymer insofar as it can be used for conventional cosmetic compositions. Any one of nonionic polymers, amphoteric polymers, anionic polymers, cationic polymers, and natural polysaccharides and derivatives thereof can be used.

Specific examples of the nonionic polymer include polyvinyl alcohol; polyvinyl pyrrolidone polymers such as polyvinyl pyrrolidone ["Luviskol K12" and "Luviskol K13" (each, trade name; product of BASF AG, "PVP K15" and "PVP K30" (each, trade name; product of GAF Corp.) and the like], polyvinyl pyrrolidone/vinyl acetate copolymers ["Luviskol VA28" and "Luviskol VA73" (each, trade name; product of BASF AG, "PVP/VAE-735" and "S-630" (each, trade name; product of GAF Corp.) and the like], polyvinyl pyrrolidone/vinyl acetate/vinyl propionate terpolymer ["Luviskol VAP343", trade name; product of BASF) and the like], polyvinyl pyrrolidone/alkylamino acrylate copolymers ["Luviflex", trade name; product of BASF AG), "Copolymer 845", "Copolymer 937" and "Copolymer 958" [trade name; product of GAF Corp.)] and the like], polyvinyl pyrrolidone/acrylate/(meth)acrylic acid copolymers ["Luviflex VBM35" (trade name; product of BASF AG) and the like], and polyvinyl pyrrolidone/alkylamino acrylate/vinyl caprolactam copolymers ["Copolymer VC-713" (trade name; product of GAF Corp.) and the like]; and high-polymeric polyethylene glycols such as polyethylene glycol 20000000 ["Polyox WSR N-60K" (trade name; product of Union Carbide Corp. and the like].

Specific examples of the amphoteric polymer include amphoteric acrylic polymers such as dialkylaminoethyl (meth)acrylate/alkyl (meth)acrylate copolymers ["Yukaformer M-75" and "Yukaformer SM" (each, trade name; product of Mitsubishi Petrochemical Co., Ltd.) and the like] and hydroxypropyl acrylate/butylaminoethyl methacrylate/octylamide acrylate copolymers ["Amformer 28-4910" (trade name; product of National Starch Inc.) and the like].

Specific examples of the anionic polymer include acidic acrylic acid polymers such as (meth)acrylic acid/(meth) acrylate ester copolymers ["Plus Size L53P" (trade name; GOO Chemical Co., Ltd.), "Diahold" (trade name; product of Mitsubishi Petrochemical Co., Ltd.) and the like], acrylic acid/alkyl acrylate/alkyl acrylamide copolymers ["Ultrahold 8" (trade name; product of BASF AG), "Amformer V-42" (National Starch Inc.) and the like] and ethyl acrylate/methyl methacrylate/methacrylic acid/acrylic acid copolymers ["Amahold DR-25" (trade name; product of Union Carbide Corp.) and the like]; vinyl acetate ether polymers such as methyl vinyl ether/anhydrous alkyl maleimide half-ester copolymers ["Gantrez ES-225", "Gantrez ES-425", "Gantrez ES-335" and "Gantrez SP-215" (each, trade name; product of GAF Corp.) and the like]; basic acrylic polymers such as acrylamide.acryl ester quadripolymers [those described in Japanese Patent Laid-Open No. HEI 2-180911]; water-dispersible polyester resins such as diethylene glycol.cyclohexane dimethanol.isophthalic acid-sulfoisophthalic acid condensate ["Eastman AQ-38S" and "Eastman AQ-55S" (each, trade name; product of Eastman Chemical Products) and the like]; and acidic polyvinyl acetate polymers such as vinyl acetate/crotonic acid copolymers ["Resin 28-1310" (trade name; product of National Starch Inc.), "Luviset CA66" (trade name; product of BASF) and the like], vinyl acetate/crotonic acid/vinyl neodecanoate copolymers ["Resin 28-2930" (National Starch Inc.) and the like] and vinyl acetate/crotonic acid/vinyl propionate copolymers ["Luviset CAP", trade name; product of BASF) and the like].

Specific examples of the cationic polymer include (quaternized) vinylpyrrolidone (meth)acrylate/amino alcohol copolymers ["Gafquat 734", and "Gafquat 755" (each, trade name; product of GAF Corp.), "Copolymer 845" (GAF Corp.) and the like]; cationic cellulose derivatives ["Cellquat L-200", "Cellquat H-100" and "Cellquat H-60" (each, trade name; product of National Starch, Inc.), "Quaternary Soft Polymer LM-200" (trade name; product of Union Carbide Corp.), "Polymer JR-400", "Polymer JR-125" and "JR30M" (each, trade name; product of Union Carbide), "Jaguar C-13" (Cellanies Inc) and the like]; and dimethyl diallyl ammonium chloride derivatives such as dimethyl diallyl ammonium chloride polymers ["Merquat 100" (trade name; product of Merck & Co., Inc.) and the like] and dimethyldiallyl ammonium chloride/acrylamide copolymers ["Merquat 550" (trade name; product of Merck & Co., Inc.) and the like].

Specific examples of the natural polysaccharide and its derivative include celluloses such as cellulose gum, for example, carboxycellulose sodium salt, cetylhydroxyethyl cellulose, hydroxyethyl cellulose, hydroxypropylmethyl cellulose, hydroxypropyl cellulose, methyl cellulose, ethyl cellulose, crystalline cellulose and carboxymethyl cellulose/salt; chitin.chitosan derivatives such as hydroxypropyl chitosan ["Chitofilmer", trade name; product of Ichimaru Falcos Co., Ltd.) and the like], carboxymethyl chitin, carboxymethyl chitosan and salts between chitosan and a monovalent or divalent acid [chitosan.pyrrolidone carboxylate salt, chitosan.lactate salt, chitosan.glycolate salt, chitosan.adipate salt, chitosan.succinate salt and the like]; carrageenan; and gum arabic, acacia gum, amylose, corn starch (amylopectin and the like), dextrin, gum karaya, pectin, sclerotiorin gum, gum tragacanth, xanthane gum, rocust bean gum, guar gum, hydroxypropyl guar gum, sodium hyarolonate, arginine, arginate salt ["Texamine 558" and "Texaine 778" (each, trade name; product of Henkel and the like], soluble starch, dialdehyde starch, starch, starch phosphate ester, angelica gum, arabinogalactan, tamarind, phaseolin, galactan, mannan and pullulan.

Among these polymers, polyethylene glycol 20000000, dialkylaminoethyl (meth)acrylate/alkyl (meth)acrylate copolymers and hydroxypropyl chitosan are particularly preferred.

These polymers can be used either singly or in combination. It is preferred to add it in an amount of 0.001 to 20 wt. % based on the total weight of the composition, with 0.01 to 10 wt. % being particularly preferred and with 0.1 to 5 wt. % being still more preferred.

To the he hair cosmetic composition of the present invention, a penetration enhancer can be added further. It can impart hair with more suppleness and therefore, the addition of it is preferred. No particular limitation is imposed on the penetration enhancer insofar as it can be used for the conventional cosmetic compositions. As the penetration enhancer, the following organic solvents represented by the following formula (32) or (33) can be given as examples.

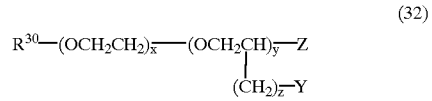 (32)

wherein $R^{30}$ represents a hydrogen atom, a linear or branched $C_{1-4}$ alkyl group, a group

or a group

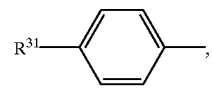, in which $R^{31}$ represents a hydrogen atom, a methyl group or a methoxy group and $R^{32}$ represents —$CH_2$—, —$(CH_3)_2$—, —$CH_2CH_2$—, —$CH_2CH(CH_3)$—, —$CH_2CH_2CH_2$— or —$CH$=$CHCH_2$—, x, y and z individually represent an integer of 0 to 5, Y and Z individually represent a hydrogen atom or a hydroxyl group, with the proviso that when $R^{30}$ and Z represent a hydrogen atom at the same time, the following equation: x=y=z=0 does not hold.

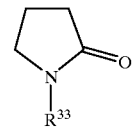 (33)

wherein $R^{33}$ represents a linear or branched $C_{1-18}$ alkyl group.

Specific examples of the organic solvent include ethanol, isopropanol, n-propanol, n-butanol, isobutanol, ethylene glycol, propylene glycol, 1,3-butanediol, benzyl alcohol, cinnamyl alcohol, phenetyl alcohol, p-anisyl alcohol, p-methylbenzyl alcohol, phenoxy ethanol, 2-benzyloxyethanol, methyl carbitol, ethyl carbitol, propylcarbitol, butyl carbitol, triethylene glycol monoethyl ether, triethylene glycol monobutyl ether and glycerin; pyrrolidone derivatives such as N-methylpyrrolidone, N-hexylpyrrolidone, N-octylpyrrolidone and N-laurylpyrrolidone.

Among them, isopropanol, n-propanol, benzyl alcohol, 2-benzyl oxyethanol and pyrrolidone derivatives are preferred.

The above penetration enhancers can be used either singly or in combination. It is preferred to add it in an amount of 0.001 to 20 wt. % based on the total amount of the composition, with 0.01 to 10 wt. % being particularly preferred and with 0.1 to 5 wt. % being still more preferred.

In the hair cosmetic composition of the present invention, it is possible to incorporate as needed, in addition to the above-described ingredients, other ingredients conventionally added to the cosmetic compositions within an extent not impairing the advantages of the present invention. Examples of such ingredients include pharmaceutically effective agents such as surfactant, anti-dandruff, insecticide and vitamin, antiseptics such as paraben, colorants such as dye and pigment, ultraviolet absorbers, vegetable extracts, astringents, amino acids, proteins, proteolytic products, blood circulation enhancers, humectants, hair growth enhancers, hair nourishments, singlet oxygen eliminators, antioxidants, perfumes and coloring matters.

The hair cosmetic compositions according to the present invention embrace all the cosmetic compositions applied to hair, for example, pre-shampoo treatment agent, shampoo, hair rinse, hair conditioner, hair treatment, setting lotion, blow styling lotion, hair spray, foam styling agent, gel styling agent, hair liquid, hair tonic, hair cream, hair growth accelerator, hair nourishment, 1st component for permanent wave, 2nd component for permanent wave, permanent hair dye and temporary hair dye.

It is possible to provide the hair cosmetic composition of the present invention in various forms according to applications, such as aqueous solution, ethanol solution, emulsion, suspension, gel, liquid crystal, solid and aerosol.

EXAMPLES

The present invention will hereinafter be described on the basis of the following examples. It is however to be borne in mind that the present invention is not limited to or by the following examples. In Preparation Example 1 to 10, the amide derivatives (1) were prepared following the above-described Preparation Process 1.

Preparation Example 1

In a 2-liter five-necked flask fitted with a stirrer, a dropping funnel, a nitrogen inlet tube and a distillation equipment, 743.2 g (8.34 mol) of 3-methoxypropylamine and 150 ml of ethanol were charged and, while the resulting mixture was stirred under heat at 80° C. under a nitrogen atmosphere, 165.9 g (0.56 mol) of hexadecyl glycidyl ether were added dropwise to the mixture over 3 hours. After completion of the dropwise addition, the reaction mixture was stirred at 80° C. for 12 hours and the ethanol and excess 3-methoxypropylamine were distilled out under heat and reduced pressure. The residue was purified by chromatography on a silica gel column, whereby 196.5 g of an amino alcohol derivative (4a) were obtained (yield: 91% based on the hexadecyl glycidyl ether) (step 1).

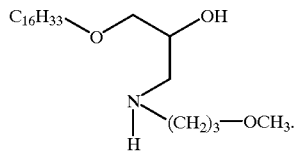
(4a)

In a 1-liter five-necked flask fitted with a stirrer, a dropping funnel, a nitrogen inlet tube and a distillation equipment, 61.3 g (158.1 mmol) of the compound (4a), which had been obtained above (step 1) and had been molten, and 1.53 g (7.91 mmol) of a 28% methanol solution of sodium methoxide were charged, followed by stirring at 60° C. for 30 minutes under a nitrogen atmosphere. Under the same conditions, 38.3 g (158.1 mmol) of methyl tetradecanoate were added dropwise to the resultant mixture over 1 hour. After completion of the dropwise addition, the reaction mixture was stirred at 60° C. for 5 hours under reduced pressure (80–10 Torr) so that the reaction was brought to completion. The reaction mixture was cooled and then purified by chromatography on a silica gel column, whereby 88.7 g of an amide derivative (2a) were obtained (yield: 94%) (step 2).

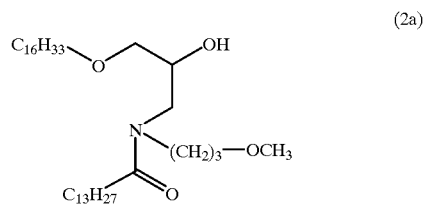
(2a)

In a 1-liter five-necked flask fitted with a stirrer, a nitrogen inlet tube and a distillation equipment, 94.5 g (158.0 mmol) of the compound (2a) obtained above (step 2), 1.53 g (4.74 mmol) of tetrabutylammonium bromide, 32.2 g (347.6 mmol) of epichlorohydrin, 12.6 g (315.0 mmol) of sodium hydroxide and 66 ml of toluene were charged, followed by stirring at 45° C. for 10 hours under a nitrogen atmosphere. After the reaction mixture so obtained was washed three times at 70° C. with water, the toluene and excess epichlorohydrin were distilled out under heat and reduced pressure and the residue was purified by chromatography on a silica gel column, whereby 94.9 g of an amide derivative (3a) were obtained (yield: 92%) (step 5).

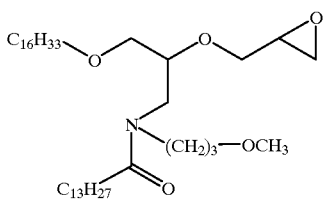
(3a)

Into a 100-ml autoclave fitted with a stirrer, 71.3 g (109.0 mmol) of the compound obtained above (step 5), 11.78 g (654.1 mmol) of water, 0.087 g (2.18 mmol) of sodium hydroxide and 0.87 g (4.36 mmol) of tetradecanoic acid were charged, followed by stirring at 160° C. for 6 hours in a closed system. After the reaction mixture was cooled, it was washed twice at 80° C. with a 2% aqueous solution of NaCl and then purified by chromatography on a silica gel column, whereby 68.3 of a target amide derivative (1a) were obtained (yield: 93%) (step 6).

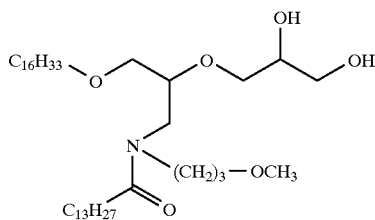
(1a)

Into a 500-ml four-necked flask fitted with a stirrer, a nitrogen inlet tube and a distillation equipment, 31.0 g (47.4 mmol) of the compound (3a) obtained above (step 5), 11.9 g (663.7 mmol) of water, 13.6 g (165.9 mmol) of sodium acetate and 104.9 g (1746.8 mmol) of acetic acid were charged, followed by stirring at 70° C. for 19 hours under a nitrogen atmosphere. Excess acetic acid was distilled out under heat and reduced pressure, whereby a mixture containing ester-amide derivatives (14a-1), (14a-2) and (14a-3) were obtained (step 7).

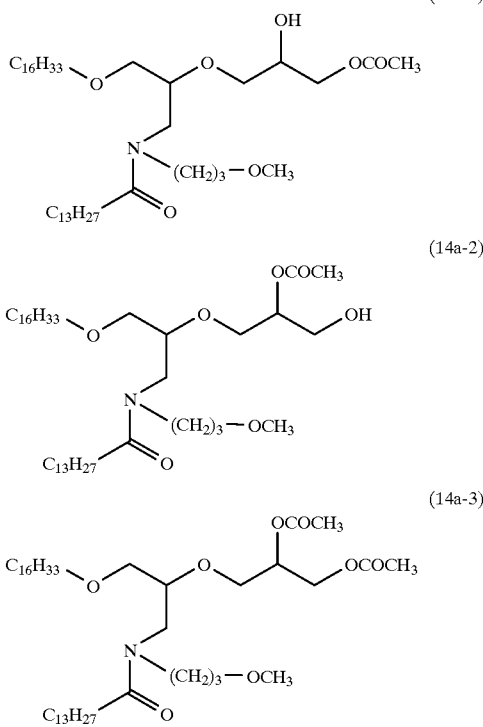

The mixture containing those ester-amide derivatives, without being taken out of the flask, were next added with 59.3 g (711.2 mmol) of a 48% aqueous solution of sodium hydroxide, 18 g of water and 200 ml of butanol, followed by stirring at 80° C. for 3 hours. The butanol was distilled out under heat and reduced pressure. After the residue was diluted in 250 ml of toluene, the resultant solution was washed twice at 70° C. with water. The toluene was distilled out under heat and reduced pressure and the residue was purified by chromatography on a silica gel column, whereby 22.3 g of the intended amide derivative (1a) were obtained (yield: 70%) (step 8).

Preparation Example 2

Into a 10-liter five-necked flask fitted with a stirrer, a dropping funnel, a nitrogen inlet tube and a distillation equipment, 4680 g (52.5 mol) of 3-methoxypropylamine and 900 g of ethanol were charged and, while the resulting mixture was stirred at 80° C. under heat and a nitrogen atmosphere, 1045 g (3.50 mol) of hexadecyl glycidyl ether were added dropwise to the mixture over 3 hours. After completion of the dropwise addition, the reaction mixture was stirred at 80° C. for 1 hour and the ethanol and excess 3-methoxypropylamine were distilled out under heat and reduced pressure, whereby a product composed of an amino alcohol derivative (4a) as a principal component was obtained (step 1).

To the product obtained above (step 1), which was composed of the compound (2a) as the principal component and was contained in the 10-liter five-necked flask, 9.82 g (0.175 mol) of potassium hydroxide were added. Under ebullation of nitrogen, the resultant mixture was stirred under reduced pressure (60 to 100 Torr) at 80° C. for 3 hours while distilling out the resulting water. With stirring under the same conditions, 882.3 g (3.64 mol) of methyl tetradecanoate were next added dropwise to the reaction mixture over 3 hours. During the dropwise addition, the resulting methanol was distilled out. After completion of the dropwise addition, the mixture was stirred under ebullation of nitrogen and reduced pressure (60 to 10 Torr) at 60 to 45° C. for 10 hours while distilling out the resulting methanol, whereby the reaction was brought to completion and a compound composed of an amide derivative (2a) as a principal component was obtained (step 2).

To the product obtained above (step 2), composed of the compound (2a) as the principal component and contained in the 10-liter five-necked flask, 33.9 g (0.105 mol) of tetrabutylammonium bromide, 712.5 g (7.70 mol) of epichlorohydrin and 2100 g of toluene were added. Under ebullation of nitrogen, 1750.0 g (21.0 mol) of a 48% aqueous solution of sodium hydroxide were added dropwise under reduced pressure (150 to 50 Torr) at 45° C. with stirring over 2 hours. After completion of the dropwise addition, the resultant mixture was stirred for 10 hours under the same conditions to bring the reaction to completion. After the reaction mixture was washed four times at 70° C. with water, the toluene and excess epichlorohydrin were distilled out under heat and reduced pressure, whereby a product composed of an amide derivative (3a) as a principal component was obtained (step 5).

To the product obtained above (step 5), composed of the compound (3a) as the principal component and contained in the 10-liter five-necked flask, 378.2 g (21.0 mol) of water, 5.83 g (0.070 mol) of a 48% aqueous solution of sodium hydroxide and 32.0 g (0.14 mol) of tetradecanoic acid were added, followed by stirring at 100° C. for 2.5 days under a nitrogen atmosphere. After the reaction mixture was washed three times at 80° C. with a 2% aqueous solution of NaCl, water was eliminated under heat and reduced pressure, whereby 2261.5 g of a product composed of a target compound (1a) as a principal component were obtained (step 6). The product contained the compound (1a) in an amount of 70% and in addition, also contained intermediates, reaction byproducts and the like represented by the following formulae:

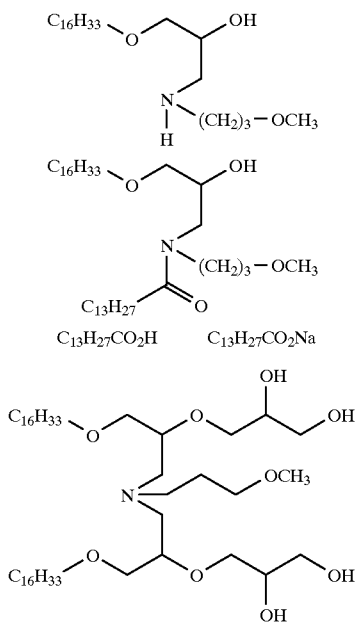

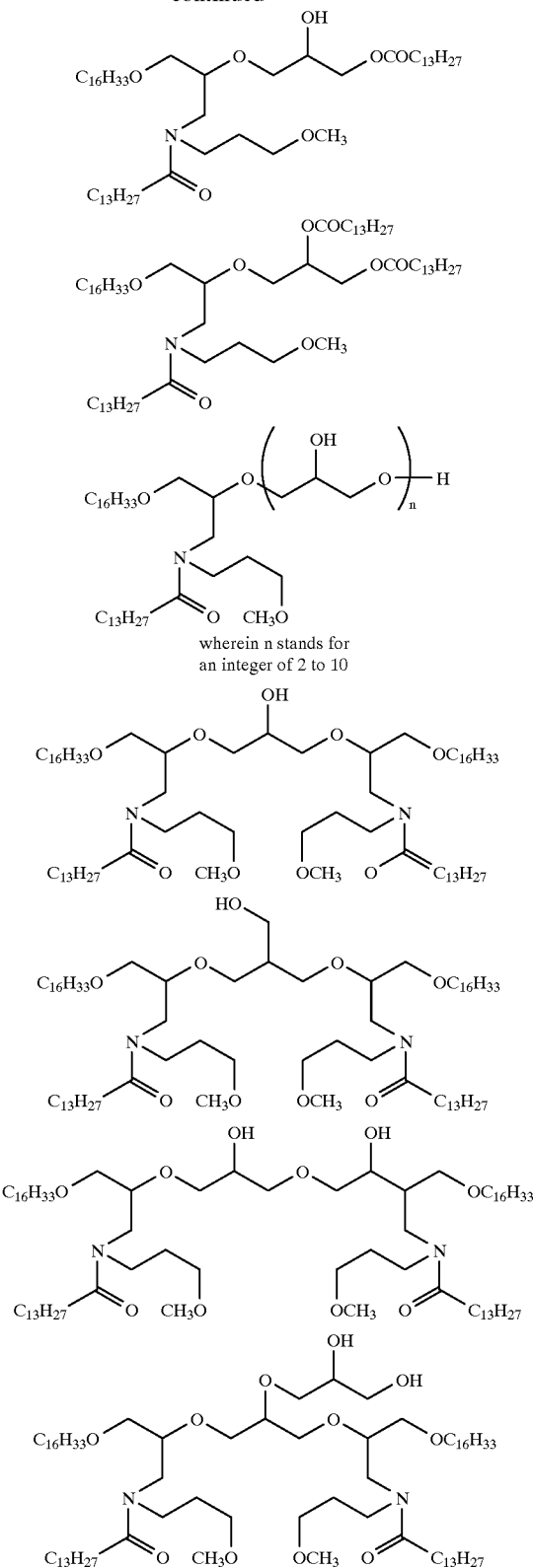

Preparation Example 3

An amide derivative (2b) was obtained by conducting reactions as in steps 1 and 2 of Preparation Example 1 except that in step 2 of Preparation Example 1, methyl hexade-canoate was used in lieu of methyl tetradecanoate (steps 1 and 2).

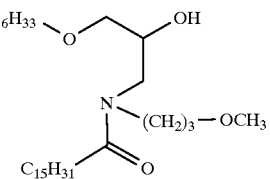

An amide derivative (3b) was obtained by conducting a reaction as in step 5 of Preparation Example 1 except that in step 5 of Preparation Example 1, the compound (2b) obtained above (step 2) was used in lieu of the compound (2a) (step 5).

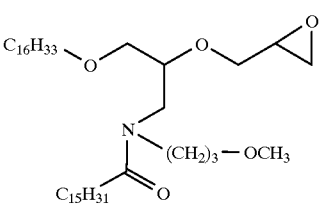

A target amide derivative (1b) was obtained by conducting a reaction as in step 6 of Preparation Example 1 except that in step 6 of Preparation Example 1, the compound (3b) obtained above (step 5) was used in lieu of the compound (3a) and hexadecanoic acid was employed in place of tetradecanoic acid (step 6).

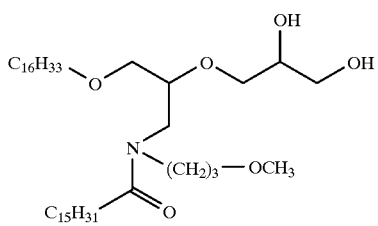

Into a 500-ml four-necked flask fitted with a stirrer and a nitrogen inlet tube, 34.1 g (50.0 mmol) of the compound (3b) obtained above (step 5), 25.5 g (250.0 mmol) of acetic anhydride and 25.3 g (250.0 mmol) of triethylamine were charged, followed by stirring at 100° C. for 10 hours under a nitrogen atmosphere. The reaction mixture was concentrated under heat and reduced pressure and the residue so obtained was purified by chromatography on a silica gel column, whereby 34.9 g of an ester-amide derivative (14b) were obtained (yield: 89%) (step 7).

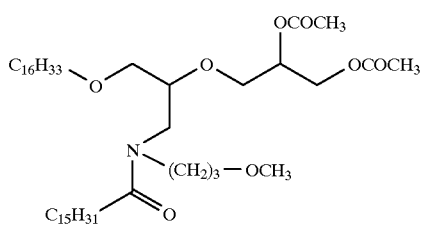

(14b)

Into a 200-ml four-necked flask fitted with a stirrer and a nitrogen inlet tube, 33.9 g (43.2 mmol) of the compound (14b) obtained above (step 7), 0.42 g (2.16 mmol) of a 28% methanol solution of sodium methoxide and 200 ml of methanol were charged, followed by stirring at room temperature for 3.5 hours under a nitrogen atmosphere. The reaction mixture was concentrated under heat and reduced pressure and the residue so obtained was purified by chromatography on a silica gel column, whereby 16.0 g of a target amide derivative (1b) were obtained (yield: 53%) (step 8).

Into a 3-liter four-necked flask fitted with a stirrer and a nitrogen inlet tube, 45.2 g (72.0 mmol) of the compound (2b) obtained above (step 2), 2.86 g (119.2 mmol) of sodium hydride and 800 ml of toluene were charged, followed by stirring at 55° C. for 30 minutes under a nitrogen atmosphere. Next, 34.8 g (121.5 mmol) of 1,2-isopropylidenedioxy-3-tosyloxypropane were added to the resultant mixture, followed by stirring at 100° C. for 18 hours. The reaction mixture was added under ice cooling with 20 ml of 2-propanol to inactivate unreacted sodium hydride and was then concentrated under heat and reduced pressure. The residue so obtained was purified by chromatography on a silica gel column, whereby 51.0 g of a 1,3-dioxolane-amide derivative (16b) were obtained (yield: 96%) (step 11).

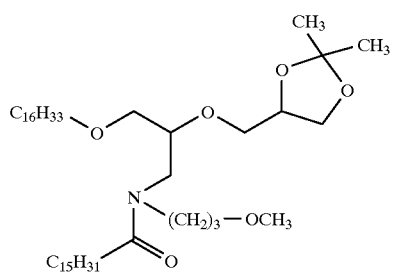

(16b)

Into a 2-liter four-necked flask fitted with a stirrer and a nitrogen inlet tube, 51.0 g (68.9 mmol) of the compound (16b) obtained above (step 11), 0.50 g (2.63 mmol) of tosyl acid monohydrate and 500 ml of methanol were charged, followed by stirring at room temperature for 12 hours under a nitrogen atmosphere. The reaction mixture was concentrated under heat and reduced pressure and the residue so obtained was purified by chromatography on a silica gel column, whereby 41.0 g of a target amide derivative (1b) was obtained (yield: 85%) (step 10).

Preparation Example 4

An amide derivative (2c) was obtained by conducting reactions as in step 1 and step 2 of Preparation Example 1 except that in step 2 of Preparation Example 1, methyl dodecanoate was used instead of methyl tetradecanoate (steps 1 and 2).

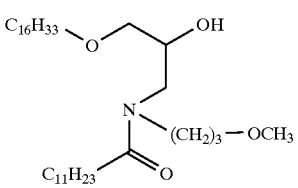

(2c)

An amide derivative (3c) was obtained by conducting a reaction as in step 5 of Preparation Example 1 except that in step 5 of Preparation Example 1, the compound (2c) obtained above (step 2) was used in lieu of the compound (2a) (step 5).

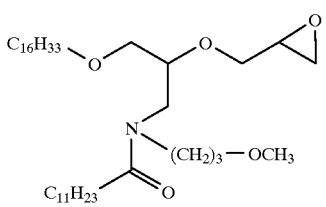

(3c)

A target amide derivative (1c) was obtained by conducting reactions as in step 7 and step 8 of Preparation Example 1 except that in step 7 of Preparation Example 1, the compound (3c) obtained above (step 5) was used instead of the compound (3a) (steps 7 and 8).

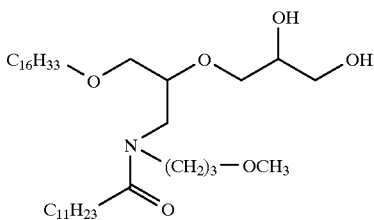

(1c)

Preparation Example 5

An amide derivative (2d) was obtained by conducting reactions as in step 1 and step 2 of Preparation Example 1 except that in step 2 of Preparation Example 1, the methyl ester of "Lunac P-70" (trade name for a 3:70:27 mixture by weight ratio of tetradecanoic acid, hexadecanoic acid and octadecanoic acid; product of Kao Corporation), which ester had been prepared by reacting "Lunac P-70" with methanol in the presence of sulfuric acid as a catalyst under heat and reflux, was used in place of methyl tetradecanoate (steps 1 and 2).

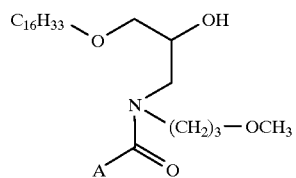

(2d)

wherein A represents a mixture of $C_{13}H_{27}$, $C_{15}H_{31}$ and $C_{17}H_{35}$.

A target amide derivative (1d) was obtained by conducting reactions as in step 11 and step 10 of Preparation Example 3 except that in step 11 of Preparation Example 3, the reaction was conducted using the compound (2d), which had been obtained above (step 2), instead of the compound (2b) and in the next step 10, the reaction was conducted without purification of the thus-obtained 1,3-dioxolaneamide derivative (16d) (steps 11 and 10).

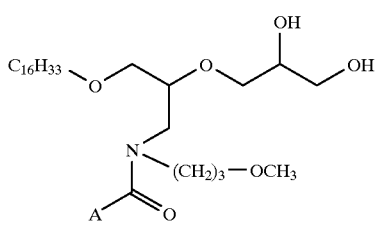

(1d)

wherein A represents a mixture of $C_{13}H_{27}$, $C_{15}H_{31}$ and $C_{17}H_{35}$.

Preparation Example 6

An amino alcohol derivative (4e) was obtained by conducting a reaction as in step 1 of Preparation Example 1 except that in step 1 of Preparation Example 1, octadecyl glycidyl ether was used instead of hexadecyl glycidyl ether (step 1).

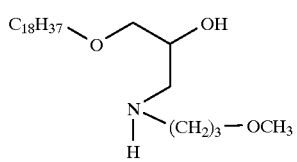

(4e)

An amide derivative (2e) was obtained by conducting a reaction as in step 2 of Preparation Example 1 except that in step 2 of Preparation Example 1, the compound (4e) obtained above (step 1) was used in lieu of the compound (4a) (step 2).

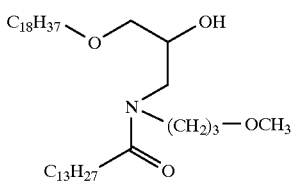

(2e)

An amide derivative (3e) was obtained by conducting a reaction as in step 5 of Preparation Example 1 except that in step 5 of Preparation Example 1, the compound (2e) obtained above (step 2) was used instead of the compound (2a) (step 5).

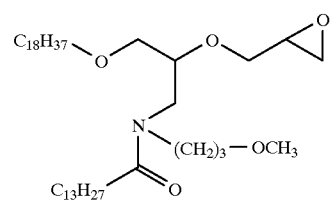

(3e)

A target amide derivative (1e) was obtained by conducting reactions as in steps 7 and 8 of Preparation Example 1 except that in step 7 of Preparation Example 1, the compound (3e) obtained above (step 5) was used instead of the compound (3a) (steps 7 and 8).

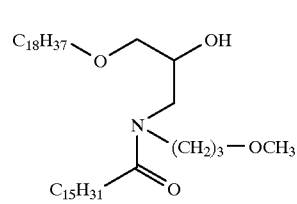

(1e)

Preparation Example 7

An amide derivative (2f) was obtained by conducting a reaction as in step 2 of Preparation Example 1 except that in step 2 of Preparation Example 1, the compound (4e) obtained in step 1 of Preparation Example 6 was used instead of the compound (4a) and methyl hexadecanoate was employed in place of methyl tetradecanoate (steps 1 and 2).

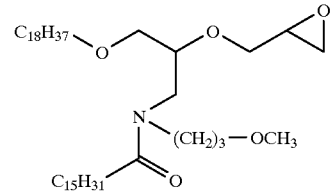

(2f)

An amide derivative (3f) was obtained by conducting a reaction as in step 5 of Preparation Example 1 except that in step 5 of Preparation Example 1, the compound (2f) was used instead of the compound (2a) (step 5).

(3f)

A target amide derivative (1f) was obtained by conducting reactions as in steps 7 and 8 of Preparation Example 1 except that in step 7 of Preparation Example 1, the compound (3f) obtained above (step 5) was used instead of the compound (3a) (steps 7 and 8).

pound (3g) obtained above (step 5) was used instead of the compound (3a) (steps 7 and 8).

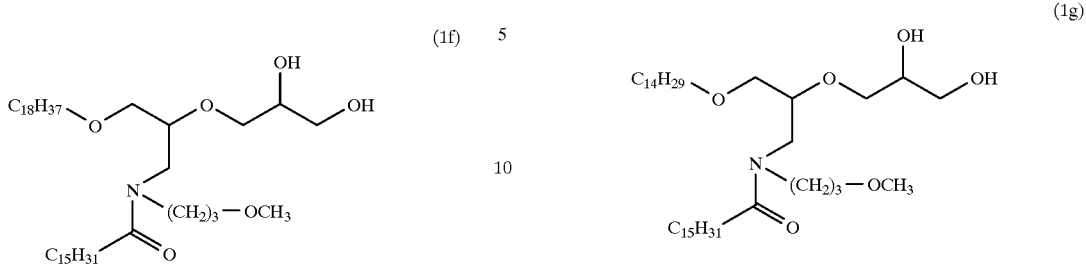

Preparation Example 8

An amino alcohol derivative (4g) was obtained by conducting a reaction as in step 1 of Preparation Example 1 except that in step 1 of Preparation Example 1, tetradecyl glycidyl ether was employed in lieu of hexadecyl glycidyl ether (step 1).

Preparation Example 9

An amino alcohol derivative (4h) was obtained by conducting a reaction as in step 1 of Preparation Example 1 except in step 1 of Preparation Example 1, 2-methoxyethylamine was used instead of 3-methoxypropylamine (step 1).

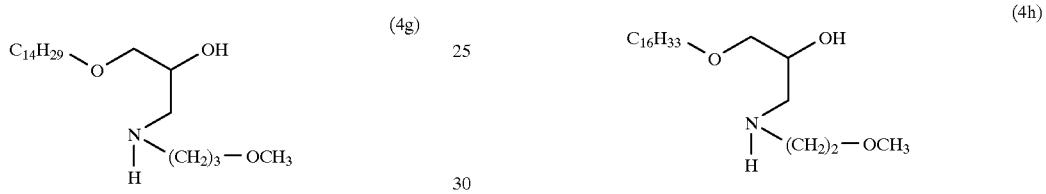

An amide derivative (2g) was obtained by conducting a reaction as in step 2 of Preparation Example 1 except that in step 2 of Preparation Example 1, the compound (4g) obtained above (step 1) was used instead of the compound (4a) and methyl hexadecanoate was used in place of methyl tetradecanoate (step 2).

An amide derivative (2h) was obtained by conducting a reaction as in step 2 of Preparation Example 1 except that in step 2 of Preparation Example 1, the compound (4h) obtained above (step 1) was used instead of the compound (4a) and methyl hexadecanoate was used in place of methyl tetradecanoate (step 2).

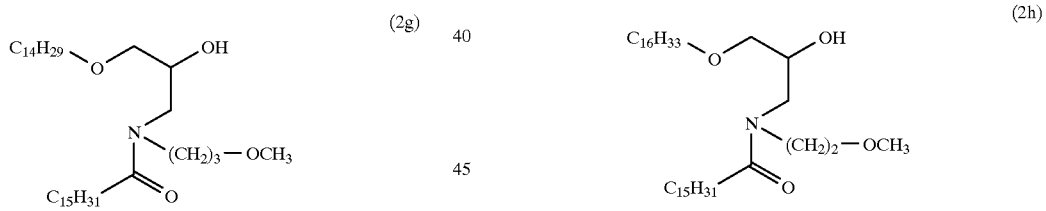

An amide derivative (3g) was obtained by conducting a reaction as in step 5 of Preparation Example 1 except that in step 5 of Preparation Example 1, the compound (2g) obtained above (step 2) was used instead of the compound (2a) (step 5).

An amide derivative (3h) was obtained by conducting a reaction as in step 5 of Preparation Example 1 except that in step 5 of Preparation Example 1, the compound (2h) obtained above (step 2) was used instead of the compound (2a) (step 5).

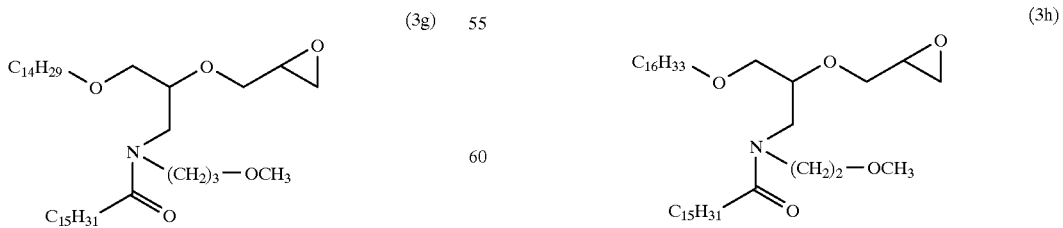

A target amide derivative (1g) was obtained by conducting reactions as in steps 7 and 8 of Preparation Example 1 except that in step 7 of Preparation Example 1, the com- A target amide derivative (1h) was obtained by conducting a reaction as in step 6 of Preparation Example 1 except that in step 6 of Preparation Example 1, the compound (3h)

obtained above (step 5) was used instead of the compound (3a) (step 6).

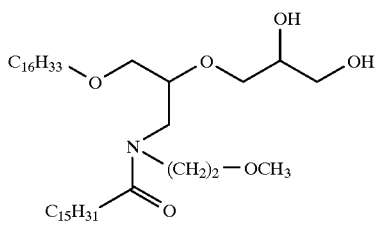
(1h)

A 1,3-dioxolane-amide derivative (16h) was obtained by conducting a reaction as in step 11 of Preparation Example 3 except that in step 11 of Preparation Example 3, the compound (2h) obtained above (step 2) was used instead of the compound (2b) (step 11).

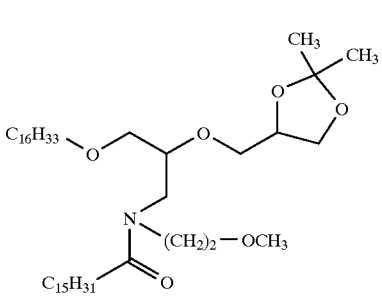
(16h)

A target amide derivative (1h) was obtained by conducting a reaction as in step 11 of Preparation Example 3 except that in step 10 of Preparation Example 3, the compound (16h) obtained above (step 11) was used instead of the compound (16b) (step 10).

Preparation Example 10

An amino alcohol derivative (4i) was obtained by conducting a reaction as in step 1 of Preparation Example 1 except that in step 1 of Preparation Example 1, ethylamine was used instead of 3-methoxypropylamine (step 1).

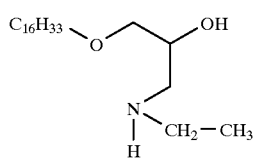
(4i)

An amide derivative (2i) was obtained by conducting a reaction as in step 2 of Preparation Example 1 except that in step 2 of Preparation Example 1, the compound (4i) obtained above (step 1) was used instead of the compound (4a) and methyl hexadecanoate was used in place of methyl tetradecanoate (step 2).

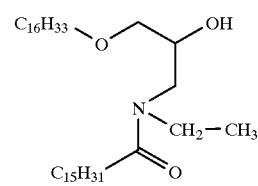
(2i)

An amide derivative (3i) was obtained by conducting a reaction as in step 5 of Preparation Example 1 except that in step 5 of Preparation Example 1, the compound (2i) obtained above (step 2) was used instead of the compound (2a) (step 5).

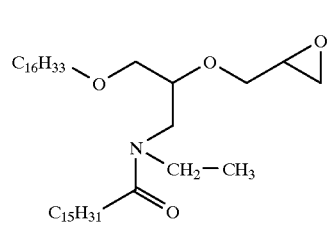
(3i)

A target amide derivative (1i) was obtained by conducting a reaction as in step 6 of Preparation Example 1 except that in step 6 of Preparation Example 1, the compound (3i) obtained above (step 5) was used instead of the compound (3a) (step 6).

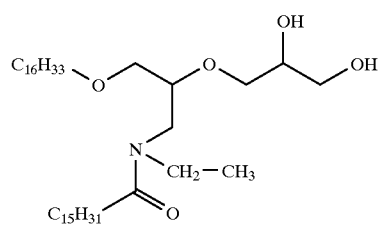
(1i)

Example 1

Hair cosmetic compositions were prepared according to Tables 1–3 in a manner known to date and touch feeling of the hair imparted by these compositions were evaluated. The results are shown in Tables 1–3.

Incidentally, the melting point as shown in Tables was measured by charging about 1 mg of a sample in the cell of a differential scanning calorimeter (DSC; 5 μl; product of Seiko Electron Industry) and heating it at the scanning temperature of 10 to 200° C. and a heating rate of 2° C./min. The extrapolation melt starting point according to JIS-K-7121-1987-9-9.1(2) was indicated as the melting point.

Evaluation Method

A bundle of the hair of about 20 cm long and about 6 g in weight was washed and then water was wiped off. The hair bundle was coated with the hair cosmetic composition to give a weight ratio of the composition to the hair of 0.1, followed by natural drying. The change of the hair in touch feeling was subjected to organoleptic evaluation by a panel of nine experts. The invention products and comparative products were evaluated by ranking them from the scores from −2 to 2 and mean values of nine experts were determined. The hair cosmetic composition with higher grades is superior.

TABLE 1

| Ingredient (wt. %) | Invention Product | | | | | | | |
|---|---|---|---|---|---|---|---|---|
| | 1 | 2 | 3 | 4 | 5 | 6 | 7 | 8 |
| Amide derivative (1a; melting point 25° C.) | 0.4 | 2.0 | 5.0 | 0.4 | 2.0 | 5.0 | 0.4 | 2.0 |
| Polyoxyethylene (20EO) sorbitan monolaurate | 1.0 | 1.5 | 1.5 | 1.5 | 1.5 | 1.5 | 1.0 | 1.0 |
| 95% ethanol | 25.0 | 25.0 | 25.0 | 50.0 | 50.0 | 50.0 | 80.0 | 80.0 |
| Water | Balance | Balance | Balance | Balance | Balance | Balance | Balance | Balance |
| Smoothness finger passing | 0.6 | 1.25 | 1.45 | 0.65 | 1.15 | 1.35 | 0.55 | 1.0 |
| Suppleness | 0.45 | 0.95 | 1.6 | 0.5 | 0.85 | 1.3 | 0.5 | 1.0 |
| Styling property | 0.25 | 1.05 | 1.4 | 0.4 | 0.95 | 1.15 | 0.4 | 1.0 |

TABLE 2

| Ingredient (wt. %) | Invention Product | | | | | | | Comp Prod. |
|---|---|---|---|---|---|---|---|---|
| | 9 | 10 | 11 | 12 | 13 | 14 | 15 | 1 |
| Amide derivative (1a; melting point 25° C.) | 5.0 | 0.4 | 2.0 | 5.0 | 0.4 | 2.0 | 5.0 | — |
| Polyoxyethylene (20EO) sorbitan monolaurate | 1.0 | — | 0.5 | 0.5 | 1.0 | 1.0 | 1.0 | 1.0 |
| 95% ethanol | 80.0 | Balance | Balance | Balance | — | — | — | 25.0 |
| Water | Balance | — | — | — | Balance | Balance | Balance | Balance |
| Smoothness/finger passing | 1.35 | 0.5 | 0.8 | 1.15 | 0.5 | 1.15 | 1.4 | −0.1 |
| Suppleness | 1.45 | 0.35 | 0.75 | 1.05 | 0.85 | 0.85 | 1.55 | −0.15 |
| Styling property | 1.45 | 0.4 | 0.95 | 1.35 | 0.45 | 0.95 | 1.45 | −0.05 |

TABLE 3

| Ingredient (wt. %) | Invention Product | | | | | | |
|---|---|---|---|---|---|---|---|
| | 16 | 17 | 18 | 19 | 20 | 21 | 22 |
| (Stock solution) | | | | | | | |
| Amide derivative (1b; melting point 33° C.) | 0.8 | 2.0 | 2.0 | 2.0 | 2.0 | 2.0 | 2.0 |
| Polyoxyethylene (20EO) sorbitan monolaurate | — | — | 1.5 | 1.5 | 0.8 | 2.0 | 2.0 |
| 95% ethanol | Balance | Balance | 20.0 | 20.0 | 20.0 | 20.0 | 20.0 |
| Water | — | — | Balance | Balance | Balance | Balance | Balance |
| (Propellant) | | | | | | | |
| Liquefied petroleum gas | 100 | 100 | — | — | — | 100 | 80 |

TABLE 3-continued

| Ingredient (wt. %) | Invention Product | | | | | | |
|---|---|---|---|---|---|---|---|
| | 16 | 17 | 18 | 19 | 20 | 21 | 22 |
| Dimethyl ether | — | — | — | — | 100 | — | 20 |
| Nitrogen gas | — | — | 100 | — | — | — | — |
| Carbon dioxide gas | — | — | — | 100 | — | — | — |
| Stock solution/propellant | 50/50 | 40/60 | 99.4/0.6 | 99/1 | 70/30 | 90/10 | 90/10 |
| Smoothness/finger passing | 0.8 | 1.25 | 1.15 | 1.4 | 1.35 | 1.05 | 1.1 |
| Suppleness | 0.65 | 0.05 | 1.05 | 1.05 | 1.2 | 1.2 | 1.15 |
| Styling ease | 0.45 | 1.05 | 0.95 | 1.05 | 0.9 | 1.1 | 1.05 |

As is apparent from the results of Tables 1 to 3, the hair cosmetic composition of the present invention brought about excellent effects for improving the touch feeling of the hair and the hair treated with the composition gave a young impression.

Example 2

The hair cosmetic composition having the composition as shown in Table 4 was prepared in a manner known to date and the touch feeling of the hair treated with it was evaluated. Evaluation was made as in Example 1 by treating the hair with the composition, allowing with the ingredients to penetrate thoroughly into the hair, drying the hair and then removing a portion of the composition on the superficies of the hair. The results are shown in Table 4.

TABLE 4

| Ingredient (wt. %) | Invention Product | | | | |
|---|---|---|---|---|---|
| | 23 | 24 | 25 | 26 | 27 |
| Amide derivative (1c; melting point 25° C.) | 2.0 | 2.0 | 2.0 | 2.0 | 2.0 |
| Polyoxyethylene (20EO) sorbitan monolaurate | 1.5 | 1.0 | 1.5 | 1.5 | 1.5 |
| Stearyl trimethylammonium chloride ("Coatamine 86W", product of Kao Corp.) | — | 0.01 | — | — | — |
| Polyethylene glycol 2000000 | — | — | 0.05 | — | — |
| Carboxyvinyl polymer ("Carbopol 940", product of B. F. Goodrich) | — | — | — | 0.2 | — |
| Glycerin | — | — | — | — | 1.5 |
| 95% Ethanol | 20.0 | 20.0 | 20.0 | 20.0 | 20.0 |
| Water | Balance | Balance | Balance | Balance | Balance |
| Smoothness/finger passing | 1.05 | 1.1 | 0.95 | 1.0 | 1.05 |
| Moisturized touch feeling | 1.1 | 1.15 | 1.0 | 1.0 | 1.15 |
| Strength and body | 0.6 | 0.55 | 0.75 | 0.65 | 0.5 |

As is apparent from the results of Table 4, the hair cosmetic composition according to the present invention exhibited excellent touch feeling improving effects and suppleness imparting effects even after washing and removal of the amide compound existing on the superficies of the hair. It has thus been confirmed that the composition penetrated into the inside of the hair, thereby improving the physical properties of the hair fundamentally.

Example 3

The hair cosmetic composition having the composition as shown in Table 5 was prepared in a manner known to date and the touch feeling of the hair treated with it was evaluated. Evaluation was made as in Example 1 by treating the hair with the composition, allowing the ingredients to penetrate into the hair at 60° C. for one hour, washing and drying the hair to remove a portion of the hair cosmetic composition on the superficies of the hair. The results are shown in Table 5.

TABLE 5

| Component (wt. %) | Invention Product 28 | Invention Product 29 |
| --- | --- | --- |
| Amide derivative (1d; melting point: 32° C.) | 0.8 | 0.8 |
| Benzyloxyethanol | 5 | — |
| Polyoxyethylene (20EO) sorbitan laurate | 1.0 | 1.0 |
| Ethanol | 20 | 20 |
| Water | Balance | Balance |
| Smoothness | 1.35 | 1.0 |
| Moisturized touch feeling | 1.25 | 0.95 |
| Suppleness | 0.7 | 0.1 |
| Luster | 0.45 | −0.05 |

As is apparent from the results of Table 5, it has been confirmed that the addition of a penetration enhancer brought about a further improvement in the touch feeling and softening effects.

Test 1

The effects for restoration from damage were evaluated with regards to the hair cosmetic composition (invention product 2) prepared in Example 1. Described specifically, a damage was given to a bundle of hair about 20 cm long and about 6 g in weight by subjecting it to redox reaction three times. After washing, water was wiped off from the hair bundle and coated with the hair cosmetic composition at a weight ratio of the hair to the cosmetic composition of 0.1, followed by natural drying. The change in the touch feeling of the hair was evaluated as in Example 1. The results are shown in Table 6.

TABLE 6

|  | Untreated | After damaged | After treatment |
| --- | --- | --- | --- |
| Smoothness/finger passing | 1.5 | 0.33 | 1 |
| Moisturized touch feeling | 1.4 | 0.75 | 1.2 |
| Oily feeling | 1.17 | 0.33 | 1.5 |
| Preference for oily feeling | 1.17 | 0.5 | 1.3 |
| Strength and body | 1.33 | 0.33 | 1.3 |
| Luster | 1.42 | 0.25 | 1.3 |

As is apparent from the results of Table 6, hair was damaged by redox reaction and its touch feeling, luster, strength and body showed a marked deterioration. By the application of the hair cosmetic composition of the present invention to the damaged hair, however, the various physical properties heightened nearly to the level of the normal hair. Thus, the hair cosmetic composition of the present invention brought about excellent effects for restoration from damage.

Example 4

The hair cosmetic composition having the composition as shown in Table 4 was prepared in a manner known to date and the touch feeling of the hair treated with it was evaluated as in Example 1. The results are shown in Table 7.

TABLE 7

| Ingredient (wt.%) | Invention Product | | | |
| --- | --- | --- | --- | --- |
|  | 30 | 31 | 32 | 33 |
| Amide derivative (1e; melting point 23° C.) | 2.0 | 1.6 | 1.6 | 1.6 |

TABLE 7-continued

| Ingredient (wt.%) | Invention Product | | | |
| --- | --- | --- | --- | --- |
|  | 30 | 31 | 32 | 33 |
| Polyoxyethylene (20EO) sorbitan monolaurate | 1.4 | 1.4 | 1.4 | 1.4 |
| Polyether modified silicone ("SH3775E", product of Toray Silicone) | — | 0.4 | — | — |
| Isopropyl palmitate ("Exepearl IPP", product of Kao Corporation) | — | — | 0.4 | — |
| Neopentyl glycol dicaprate ("Estemol N-01", product of The Nisshin Oil Mills Ltd.) | — | — | — | 0.4 |
| 95% Ethanol | 23 | 23 | 23 | 23 |
| Water | Balance | Balance | Balance | Balance |
| Smoothness | 0.15 | 1.2 | 0.15 | 0.8 |
| Moisturized touch feeling | 0.1 | 0.3 | 0.7 | 0.9 |

As is apparent from the results of Table 7, the addition of an oily ingredient brought about an improvement in the touch feeling, for example, smoothness and moisturized touch feeling.

Example 5

The hair cosmetic composition having the composition as shown in Table 8 was prepared in a manner known to date and the touch feeling of the hair treated with it was evaluated as in Example 1. The results are shown in Table 8.

TABLE 8

| Ingredient (wt. %) | Invention Product | | | |
| --- | --- | --- | --- | --- |
|  | 34 | 35 | 36 | 37 |
| Amide derivative (1f; melting point 35° C.) | 2.0 | 2.0 | 2.0 | 2.0 |
| Polyoxyethylene (20EO) sorbitan monolaurate | 1.0 | 1.0 | 1.0 | 1.0 |
| Amphoteric polymer ("Yukaformer M75", product of Mitsubishi Chemical) | — | 0.2 | — | — |
| Hydroxypropyl chitosan ("Chitofilmer", product of Ichimaru Falcos) | — | — | 0.2 | — |
| Polyethylene glycol 2000000 ("Polyox WSR N-60K", product of Union Carbide) | — | — | — | 0.2 |
| 95% Ethanol | 20 | 20 | 20 | 20 |
| Water | Balance | Balance | Balance | Balance |
| Strength and body | 0.2 | 1.1 | 1.4 | 0.6 |

As is apparent from the results of Table 8, the addition of a polymer heightened the effects for imparting the hair with strength and body.

Example 6

The hair cosmetic composition having the composition as shown in Table 9 was prepared in a manner known to date and the touch feeling of the hair treated with it was evaluated as in Example 1. The results are shown in Table 9.

TABLE 9

| Ingredient (wt.%) | Invention product 38 | Comparative product 3 |
| --- | --- | --- |
| Amide derivative (1g; melting point 27° C.) | 4.0 | — |
| Carboxyvinyl polymer ("Carbopol 940", product of B. F. Goodrich) | 0.5 | 0.5 |

TABLE 9-continued

| Ingredient (wt.%) | Invention product 38 | Comparative product 3 |
|---|---|---|
| Glycerin | 20 | 20 |
| Triethanolamine | q.s. | q.s. |
| 95% Ethanol | 10 | 10 |
| Perfume, chelating agent, antiseptic | q.s. | q.s |
| Purified water | Balance | Balance |
| Smoothness | 0.9 | −0.05 |
| Moisturized touch feeling | 0.7 | 0 |

As is apparent from the results of Table 9, the hair cosmetic composition according to the present invention caused a change in the smoothness and moisturized touch feeling, thereby improving the touch feeling.

Test 2

The spilt hair appearing ratio of the hair treated with the hair cosmetic composition was evaluated.

Described specifically, the invention products 1 and 2 obtained in Example 1 and comparative product 1 were used for the test. The hair treated with each of the hair cosmetic compositions as in Example 1 and untreated hair as a control were brushed 1000 times in repetition to give mechanical damage to the hair. A spilt hair appearing ratio was determined by dividing the number of the spilt hair appeared when treated with the hair cosmetic composition with the number of the spilt hair appeared without treatment (control). The lower the spilt hair appearing ratio, the less the hair was damaged. The results are shown in Table 10.

TABLE 10

|  | Comparative Product 1 | Invention Product 1 | Invention Product 2 |
|---|---|---|---|
| Appearing ratio of spilt hair (%) | 86 | 63 | 42 |

As is apparent from the results of Table 10, the spilt hair appearing ratio of the hair treated with the hair cosmetic composition of the present invention was low, which suggested that the mechanical damage was suppressed.

Example 7

The hair cosmetic composition having the composition as shown in Table 11 was prepared in a manner known to date and the touch feeling of the hair treated with it was evaluated as in Example 1. The results are shown in Table 11.

Evaluation Method

A bundle of the hair of about 20 cm long and about 6 g in weight was washed and then water was wiped off. The hair bundle was coated with the hair cosmetic composition to give a weight ratio of the composition to the hair of 0.1, followed by natural drying. The change of the hair in touch feeling was subjected to organoleptic evaluation by a panel of nine experts. The invention products and comparative products were evaluated by ranking them from the scores from −2 to 2 and an average of nine experts were determined. The hair cosmetic composition with higher grades is superior.

A: an average not lower than 1 but not higher than 2.
B: an average not lower than 0 but lower than 1.
C: an average not lower than −1 but lower than 0.
D: an average not lower than −2 but lower than −1.

TABLE 11

| Ingredient (wt. %) | Invention Product | | | | | | |
|---|---|---|---|---|---|---|---|
|  | 39 | 40 | 41 | 42 | 43 | 44 | 45 |
| Amide derivative (1a; melting point 25° C.) | 0.4 | 0.65 | 1.05 | 2.0 | 5.0 | 0.4 | 0.65 |
| Cholesterol | 0.1 | 0.15 | 0.15 | 0.15 | 0.30 | 0.1 | 0.15 |
| Polyoxyethylene (20EO) sorbitan monolaurate | 1.0 | 1.5 | 1.5 | 1.5 | 1.5 | 1.0 | 1.5 |
| 95% Ethanol | 20.0 | 20.0 | 20.0 | 20.0 | 20.0 | Balance | Balance |
| Water | Balance | Balance | Balance | Balance | Balance | — | — |
| Smoothness with easy finger passing | 0.1 | 0.4 | 0.55 | 0.8 | 0.7 | 0.25 | 0.4 |
| Moisturized touch feeling | 0.15 | 0.35 | 0.3 | 0.65 | 0.55 | 0.3 | 0.5 |
| Strengh and body | 0.15 | 0.25 | 0.25 | 0.2 | 0.25 | 0.1 | 0.2 |
| Styling ease | 0.3 | 0.45 | 0.55 | 0.8 | 0.75 | 0.4 | 0.6 |
| Luster | 0.3 | 0.35 | 0.5 | 0.45 | 0.5 | 0.25 | 0.3 |

| Ingredient (wt. %) | Invention Product | | | | Comparative Product | |
|---|---|---|---|---|---|---|
|  | 46 | 47 | 48 | 49 | 4 | 5 |
| Amide derivative (1a; melting point: 25° C.) | 1.05 | 2.0 | 5.0 | 5.0 | — | — |
| Cholesterol | 0.15 | 0.15 | 0.30 | 1.0 | 0.1 | — |
| Polyoxyethylene (20E0) sorbitan monolurate | 1.5 | 1.5 | 1.5 | 1.5 | 1.0 | 1.0 |
| 95% Ethanol | Balance | Balance | Balance | Balance | 20.0 | Balance |
| Water | — | — | — | — | Balance | — |
| Smoothness with easy finer passing | 0.5 | 0.65 | 0.6 | 0.5 | −0.2 | 0.05 |
| Moisturized touch feeling | 0.5 | 0.65 | 0.55 | 0.5 | −0.15 | 0 |
| Strength and body | 0.3 | 0.25 | 0.3 | 0.45 | 0.05 | −0.15 |
| Styling ease | 0.55 | 0.8 | 0.75 | 0.8 | 0 | 0.1 |
| Luster | 0.3 | 0.35 | 0.3 | 0.25 | 0.2 | 0.15 |

As is apparent from the results of Table 11, the hair cosmetic composition according to the present invention had excellent effects for improving the touch feeling of the hair. It was particularly effective for improving the smoothness and finger passing of the hair and moisturized touch feeling.

Example 8

The hair cosmetic composition having the composition as shown in Table 12 was prepared in a manner known to date and the touch feeling of the hair treated with it was evaluated. Evaluation was made as in Example 7 after treating the hair as in Example 7, allowing the ingredients to penetrate thoroughly into the hair, washing and drying the hair to remove the hair cosmetic composition existing on the superficies of the hair. The results are shown in Table 12.

TABLE 12

| Ingredient (wt. %) | Invention Product | | | | | | | Comp Prod. |
|---|---|---|---|---|---|---|---|---|
|  | 50 | 51 | 52 | 53 | 54 | 55 | 56 | 6 |
| (Stock solution) |  |  |  |  |  |  |  |  |
| Amide derivative (1b; melting point 33° C.) | 0.8 | 2.0 | 2.0 | 2.0 | 2.0 | 2.0 | 2.0 | — |

TABLE 12-continued

| Ingredient | Invention Product | | | | | | | Comp Prod. |
|---|---|---|---|---|---|---|---|---|
| (wt. %) | 50 | 51 | 52 | 53 | 54 | 55 | 56 | 6 |
| Cholesterol | 0.15 | 0.15 | 0.15 | 0.15 | 0.15 | 0.15 | 0.15 | — |
| Polyoxyethylene (20EO) sorbitan monolaurate | — | — | 1.5 | 1.5 | 0.8 | 2.0 | 2.0 | 1.5 |
| 95% ethanol | Balance | Balance | 20.0 | 20.0 | 20.0 | 20.0 | 20.0 | 20.0 |
| Water | — | — | Balance | Balance | Balance | Balance | Balance | Balance |
| (Propellant) | | | | | | | | |
| Liquefied petroleum gas | 100 | 100 | — | — | — | 100 | 80 | 100 |
| Dimethyl ether | — | — | — | — | 100 | — | 20 | — |
| Nitrogen gas | — | — | 100 | — | — | — | — | — |
| Carbon dioxide gas | — | — | — | 100 | — | — | — | — |
| Stock solution/propellant | 50/50 | 40/60 | 99.4/0.6 | 99/1 | 70/30 | 90/10 | 90/10 | 50/50 |
| Smoothness/easy finger passing | 0.35 | 0.6 | 0.7 | 0.6 | 0.65 | 0.5 | 0.55 | 0 |
| Hardness | 0.45 | 0.45 | 0.55 | 0.5 | 0.55 | 0.5 | 0.5 | 0.2 |
| Styling ease | 0.2 | 0.55 | 0.5 | 0.5 | 0.5 | 0.55 | 0.6 | −0.05 |

As is apparent from the results of Table 12, the hair cosmetic composition of the present invention had excellent effects for improving the touch feeling of the hair. In addition, it imparted the hair with strength and body.

Example 9

The hair cosmetic composition having the composition as shown in Table 13 was prepared in a manner known to date and the touch feeling of the hair treated with it was evaluated as in Example 11. The results are shown in Table 13.

TABLE 13

| Ingredient (wt. %) | Invention Product | | | |
|---|---|---|---|---|
| | 57 | 58 | 59 | 60 |
| Amide derivative (1c; melting point: 25° C.) | 2.0 | 1.6 | 1.6 | 1.6 |
| Cholesterol | 0.3 | 0.3 | 0.3 | 0.3 |
| Polyoxyethylene (20EO) sorbitan monolaurate | 1.4 | 1.4 | 1.4 | 1.4 |
| Polyether modified silicone ("SH3775E", product of Toray Silicone) | — | 0.4 | — | — |
| Isopropyl palmitate ("Exepearl IPP", product of Kao Corporation) | — | — | 0.4 | — |
| Neopentyl glycol dicaprate ("Estemol N-01", product of The Nisshin Oil Mills Ltd.) | — | — | — | 0.4 |
| 95% Ethanol | 23 | 23 | 23 | 23 |
| Water | Balance | Balance | Balance | Balance |
| Change in smoothness | B | A | B | B |
| Change in moisturized touch feeling | B | B | A | B |

As is apparent from the results of Table 13, the addition of an oily ingredient brought about changes in the smoothness and moisturized touch feeling of the hair, thereby improving the touch feeling.

Example 10

The hair cosmetic composition having the composition as shown in Table 14 was prepared in a manner known to date and the touch feeling of the hair treated with it was evaluated as in Example 7. The results are shown in Table 14.

TABLE 14

| Ingredient (wt. %) | Invention Product | | | |
|---|---|---|---|---|
| | 61 | 62 | 63 | 64 |
| Amide derivative (1d; melting point 32° C.) | 2.0 | 2.0 | 2.0 | 2.0 |
| Cholesterol | 0.3 | 0.3 | 0.3 | 0.3 |
| Polyoxyethylene (20EO) sorbitan monolaurate | 1.0 | 1.0 | 1.0 | 1.0 |
| Amphoteric polymer ("Yukafoamer M75", product of Mitsubishi Chemical) | — | 0.2 | — | — |
| Hydroxypropyl chitosan ("Chitofilmer", product of Ichimaru Falcos) | — | — | 0.2 | — |
| Polyethylene glycol 2000000 ("Polyox WSR N-60K", product of Union Carbide) | — | — | — | 0.2 |
| 95% Ethanol | 20 | 20 | 20 | 20 |
| Water | Balance | Balance | Balance | Balance |
| Strength and body | B | B | A | B |

As is apparent from the results of Table 14, the effects of imparting the hair with strength and body were improved by the addition of a polymer to the cosmetic composition of the present invention.

Example 15

The hair cosmetic composition having the composition as shown below was prepared in a manner known to date and the touch feeling of the hair treated with it was evaluated. Evaluation was made as in Example 11 after treating the hair as in Example 7, allowing the ingredients to penetrate into the hair at 60° C. for one hour, washing and drying the hair to remove the hair cosmetic composition existing on the surperfices of the hair. As a result, the hair cosmetic composition of the present invention had excellent touch feeling and improving effects, particularly, on smoothness and moisturized touch feeling.

| (Ingredient) | (wt. %) |
|---|---|
| Amide derivative (1e; melting point 23° C.) | 0.8 |
| Cholesterol | 0.3 |
| Benzyloxyethanol | 1.0 |
| Polyoxyethylene (20EO) sorbitan monolaurate | 1.5 |
| Ethanol | 20 |
| Water | Balance |
| | 100.0 |

Example 16

The hair cosmetic composition having the below-described composition was prepared in a manner known to date and the touch feeling of the hair treated with it was evaluated as in Example 7. As a result, the composition had excellent effects for improving the touch feeling of the hair. In particular, it improved the smoothness and moisturized touch feeling of hair. Moreover, it imparted the hair with strength and body.

| (Ingredient) | (wt. %) |
|---|---|
| Amide derivative (1f; melting point 35° C.) | 4.0 |
| Cholesterol | 0.6 |
| Carboxyvinyl polymer ("Carbopol 940", trade name; product of B. F. Goodrich) | 0.5 |
| Glycerin | 20 |
| Triethanolamine | q.s. |
| 95% Ethanol | 10 |
| Perfume, chelating agent, antiseptic | q.s. |
| Purified water | Balance |
| | 100.0 |

Test 3

The spilt hair appearing ratio of the hair treated with the hair cosmetic composition was evaluated.

Described specifically, the invention products 39 and 40 obtained in Example 7 and comparative product 4 were used for the test. The hair was treated with each of the hair cosmetic compositions as in Example 7, followed by repetition of brushing 1000 times to give mechanical damage to the hair. A spilt hair appearing ratio was determined by dividing the number of the spilt hair appeared when treated with the hair cosmetic composition with the number of the spilt hair appeared without treatment (control). The lower the spilt hair appearing ratio, the less the hair was damaged. The results are shown in Table 15.

TABLE 15

| | Invention Product 39 | Invention Product 40 | Comparative Product 4 |
|---|---|---|---|
| Appearing ratio of spilt hair (%) | 35 | 71 | 100 |

As is apparent from the results of Table 15, the spilt hair appearing ratio of the hair treated with the hair cosmetic composition of the present invention was low, which suggested that the mechanical damage was suppressed.

The hair cosmetic composition according to the present invention can impart the hair with suppleness, improve the touch feeling and bring about spilt hair preventive effects. Concerning the touch feeling, in particular, the composition can impart the hair with natural feeling, more specifically, with moisturized feeling, finger passing ease, styling ease, luster and not greasy but good oily feeling, whereby the hair with healthy, moisturized and young impression can be obtained. These effects are produced from the property that the above-mentioned hair cosmetic composition can prevent the lift-up phenomenon of hair cuticle and retard the progress of hair damage.

Further, the hair cosmetic composition according to the present invention makes it possible to enhance the hair improvement, as well as penetration of its ingredients into the hair when repeatedly applied to the hair.

What is claimed is:

1. A hair cosmetic composition comprising an amide compound having a melting point ranging from 0–50° C., wherein the amide compound is selected from amide derivatives represented by the following formulas (1) to (3):

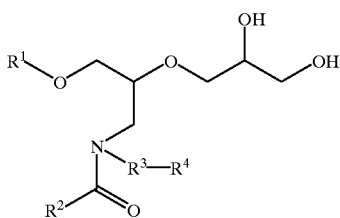
(1)

wherein $R^1$ and $R^2$ are the same or different and each independently represents a $C_{1-40}$ hydrocarbon group which may be hydroxylated, $R^3$ represents a linear or branched $C_{1-6}$ alkylene group or a single bond, and $R^4$ represents a hydrogen atom, a linear or branched $C_{1-12}$ alkoxy group or a 2,3-dihydroxypropyloxy group, with the proviso that when $R^3$ represents a single bond, $R^4$ is a hydrogen atom;

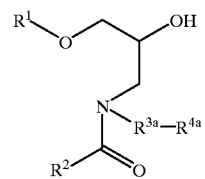
(2)

wherein $R^1$ and $R^2$ have the same meanings as defined above, $R^{3a}$ represents a linear or branched $C_{3-6}$ alkylene group, and $R^{4a}$ represents a linear or branched $C_{1-12}$ alkoxy group;

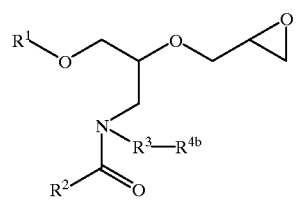
(3)

wherein $R^1$, $R^2$ and $R^3$ have the same meanings as defined above, and $R^{4b}$ represents a hydrogen atom, as linear or branched $C_{1-12}$ alkoxy group or a 2,3-epoxypropyloxy group, with the proviso that when $R^3$ represents a single bond, $R^{4b}$ is a hydrogen atom.

2. The hair cosmetic composition according to claim 1, wherein the amide compound is selected from amide derivatives each represented by the following formula (1):

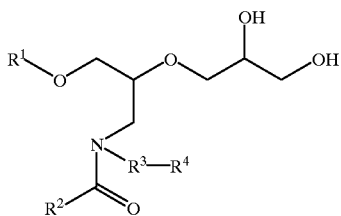

wherein $R^1$ and $R^2$ are the same or different and each independently represents a $C_{1-40}$ hydrocarbon group which may be hydroxylated, $R^3$ represents a linear or branched $C_{1-6}$ alkylene group or a single bond, and $R^4$ represents a hydrogen atom, a linear or branched $C_{1-12}$ alkoxy group or a 2,3-dihydroxypropyloxy group, with the proviso that when $R^3$ represents a single bond, $R^4$ is a hydrogen atom.

3. The hair cosmetic composition according to claim 1, wherein $R^1$ represents a linear or branched $C_{8-26}$ alkyl or alkenyl group, $R^2$ represents a linear or branched $C_{9-25}$ alkyl or alkenyl group, $R^3$ represents a linear or branched $C_{1-6}$ alkylene group, $R^4$ represents a hydrogen atom, a $C_{1-8}$ alkoxy group or a 2,3-dihydroxypropyloxy group, $R^{3a}$ represents a linear or branched $C_{3-6}$ alkylene group and $R^{4a}$ represents a $C_{1-8}$ alkoxy group.

4. The hair cosmetic composition according to claim 1, further comprising a sterol.

5. The hair cosmetic composition according to claim 4, wherein the sterol is cholesterol or a cholesterol derivative.

6. The hair cosmetic composition according to claim 1, further comprising an oily ingredient.

7. The hair cosmetic composition according to claim 6, wherein the oily ingredient is at least one member selected from the group consisting of hydrocarbons, waxes, animal or vegetable oils and fats, higher alcohols, higher fatty acids, amide amines, glycerins, esters, ethers and silicones.

8. The hair cosmetic composition according to claim 1, further comprising a polymer.

9. The hair cosmetic composition according to claim 8, wherein the polymer is at least one member selected from the group consisting of nonionic polymers, amphoteric polymers, anionic polymers, cationic polymers, and natural polysaccharides and derivatives thereof.

10. The hair cosmetic composition according to claim 1, further comprising a penetration enhancer.

11. The hair cosmetic composition according to claim 10, wherein the penetration enhancer is a compound represented by the following formula (32):

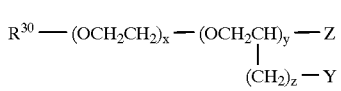

wherein $R^{30}$ represents a hydrogen atom, a linear or branched $C_{1-4}$ alkyl group, a group

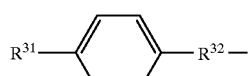

or a group

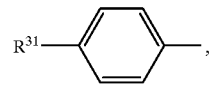

in which $R^{31}$ represents a hydrogen atom, a methyl group or a methoxy group, $R^{32}$ represents $-CH_2-$, $C(CH_3)_2-$, $-CH_2CH_2-$, $-CH_2CH(CH_3)-$, $-CH_2CH_2CH_2-$ or $-CH=CHCH_2-$, x, y and z individually represent an integer of 0 to 5, Y and Z individually represent a hydrogen atom or a hydroxyl group, with the proviso that when $R^{30}$ and Z represent a hydrogen atom at the same time, x, y and z are not all zero; or a compound represented by the formula (33):

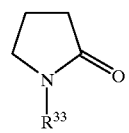

wherein $R_{33}$ represents a linear or branched $C_{1-18}$ alkyl group.

12. A process for preventing the lift-up phenomenon of hair cuticle and retarding the progress of hair damage comprising applying the composition of claim 1 to hair.

13. The process according to claim 12, wherein the amide compound is selected from amide derivatives each represented by the following formula (1):

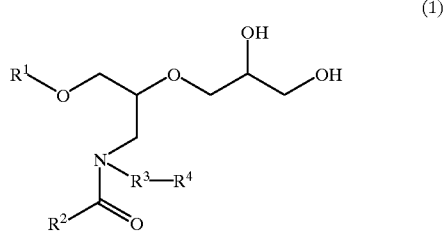

wherein $R^1$ and $R^2$ are the same or different and each independently represents a $C_{1-40}$ hydrocarbon group which may be hydroxylated, $R^3$ represents a linear or branched $C_{1-6}$ alkylene group or a single bond, and $R^4$ represents a hydrogen atom, a linear or branched $C_{1-12}$ alkoxy group or a 2,3-dihydroxypropyloxy group, with the proviso that when $R^3$ represents a single bond, $R^4$ is a hydrogen atom.

14. The hair cosmetic composition according to claim 1, wherein the amide compound is present in an amount of 0.001 to 50 wt. %, based on the composition.

15. The hair cosmetic composition according to claim 2, wherein the amide compound is present in an amount of 0.001 to 50 wt. %, based on the composition.

16. A hair cosmetic composition comprising an amide compound selected from the group consisting of isostearic acid amide, isopalmitic acid amide, isomyristic acid amide and phytostearyl acylglutamate, in an amount of 0.001 to 50 wt. %, based on the composition.

17. A process for preventing the lift-up phenomenon of hair cuticle and retarding the progress of hair damage comprising applying the composition of claim 16 to hair.

* * * * *

UNITED STATES PATENT AND TRADEMARK OFFICE
CERTIFICATE OF CORRECTION

PATENT NO. : 5,976,516
DATED : November 2, 1999
INVENTOR(S) : Masahiko Sakai, et. al.

It is certified that error appears in the above-identified patent and that said Letters Patent is hereby corrected as shown below:

Column 44, lines 50-56, delete the figure shown;
line 60, "as" should read --a--.

Signed and Sealed this

Third Day of October, 2000

Attest:

Q. TODD DICKINSON

*Attesting Officer*       *Director of Patents and Trademarks*